(12) United States Patent
Kozlov et al.

(10) Patent No.: US 9,951,101 B2
(45) Date of Patent: Apr. 24, 2018

(54) PROTEIN SEPARATIONS USING AN ACRYLAMIDE CONTAINING FILTER

(71) Applicant: EMD Millipore Corporation, Burlington, MA (US)

(72) Inventors: Mikhail Kozlov, Burlington, MA (US); William Cataldo, Burlington, MA (US); Jeffrey Caron, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 15/033,940

(22) PCT Filed: Nov. 6, 2014

(86) PCT No.: PCT/US2014/064230
§ 371 (c)(1),
(2) Date: May 3, 2016

(87) PCT Pub. No.: WO2015/088677
PCT Pub. Date: Jun. 18, 2015

(65) Prior Publication Data
US 2016/0272676 A1 Sep. 22, 2016

Related U.S. Application Data
(60) Provisional application No. 61/915,125, filed on Dec. 12, 2013.

(51) Int. Cl.
| | |
|---|---|
| *C07K 1/34* | (2006.01) |
| *C08F 220/56* | (2006.01) |
| *C08F 220/58* | (2006.01) |
| *B01D 15/10* | (2006.01) |
| *B01D 37/00* | (2006.01) |
| *B01J 20/26* | (2006.01) |
| *B01J 20/288* | (2006.01) |
| *B01J 20/289* | (2006.01) |
| *C07K 1/18* | (2006.01) |
| *C07K 16/00* | (2006.01) |
| *C08F 220/18* | (2006.01) |
| *C08F 220/54* | (2006.01) |
| *C08F 259/08* | (2006.01) |
| *C08J 5/22* | (2006.01) |

(Continued)

(52) U.S. Cl.
CPC ............... *C07K 1/34* (2013.01); *B01D 15/10* (2013.01); *B01D 37/00* (2013.01); *B01J 20/267* (2013.01); *B01J 20/288* (2013.01); *B01J 20/289* (2013.01); *B01J 20/321* (2013.01); *B01J 20/327* (2013.01); *B01J 20/3212* (2013.01); *B01J 20/3276* (2013.01); *B01J 20/3291* (2013.01); *B01J 39/26* (2013.01); *C07K 1/18* (2013.01); *C07K 16/00* (2013.01); *C08F 220/18* (2013.01); *C08F 220/54* (2013.01); *C08F 220/56* (2013.01); *C08F 220/58* (2013.01); *C08F 259/08* (2013.01); *C08J 5/2243* (2013.01); *B01J 2220/80* (2013.01); *C08F 2220/1825* (2013.01); *C08F 2220/1858* (2013.01); *C08J 2351/00* (2013.01)

(58) Field of Classification Search
CPC .. C07K 1/34; C07K 1/18; C07K 16/00; C08F 220/56; C08F 220/58; C08F 220/18; C08F 220/54; C08F 259/08; C08F 2220/1825; C08F 2220/1858; B01D 15/10; B01D 37/10; B01D 39/26; B01D 20/321; B01J 20/267; B01J 20/288; B01J 20/289; B01J 20/3212; B01J 20/327; B01J 20/321; B01J 20/3276; B01J 20/3291; B01J 39/26; B01J 2220/80; C08J 5/2243; C08J 2351/00
USPC .......................................................... 521/32
See application file for complete search history.

(56) References Cited

U.S. PATENT DOCUMENTS

| | | | |
|---|---|---|---|
| 2,788,901 | A | 4/1957 | Boeddinghaus et al. |
| 3,673,988 | A | 7/1972 | Berlin et al. |
| 4,268,463 | A | 5/1981 | Aoyagi |

(Continued)

FOREIGN PATENT DOCUMENTS

| | | |
|---|---|---|
| CN | 1882640 A | 12/2006 |
| CN | 101302504 A | 11/2008 |

(Continued)

OTHER PUBLICATIONS

International Preliminary Report on Patentability dated Jun. 23, 2016 in corresponding PCT application No. PCT/US2014/064230.
International Search Report and Written Opinion dated Feb. 10, 2015 in corresponding PCT application No. PCT/US2014/064230.
Gabrielson et al., "fluantitation of Aggregate Levels in a Recombinant Humanized Monoclonal Antibody ormulation by Size-Exclusion Chromatography, Asymmetrical Flow Field Flow Fractionation, and Sedimentation Velocity," Journal of Pharmaceutical Sciences, vol. 96, No. 2, pp. 268-279, Feb. 2007.

(Continued)

*Primary Examiner* — Michael M Bernshteyn
(74) *Attorney, Agent, or Firm* — Nields, Lemack & Frame, LLC

(57) ABSTRACT

Novel compositions for removing impurities such as, protein aggregates, from a sample containing a protein of interest, e.g., an antibody. Such compositions can be used prior to the virus filtration step during protein purification, to remove aggregates and protect the virus filter from fouling, therefore improving virus filter capacity. A porous solid support including a co-polymer having at least two monomers, wherein at least one of the monomers comprises acrylamide and at least a second monomer comprises a hydrophobic binding group, where the solid support selectively binds protein aggregates, thereby to separate the monomeric protein of interest from the protein aggregates. The method can be performed under neutral to high pH and high conductivity conditions.

10 Claims, 16 Drawing Sheets

(51) Int. Cl.
    B01J 39/26        (2006.01)
    B01J 20/32        (2006.01)

(56)            References Cited

U.S. PATENT DOCUMENTS

| | | | |
|---|---|---|---|
| 4,618,533 | A | 10/1986 | Steuck |
| 4,944,879 | A | 7/1990 | Steuck |
| 5,085,784 | A | 2/1992 | Ostreicher |
| 5,629,084 | A | 5/1997 | Moya |
| 5,906,747 | A | 5/1999 | Coffman et al. |
| 3,039,872 | A | 3/2000 | Wu et al. |
| 6,365,395 | B1 | 4/2002 | Antoniou |
| 6,620,918 | B2 | 9/2003 | Ansaldi et al. |
| 6,783,937 | B1 | 8/2004 | Hou et al. |
| 6,849,185 | B1 | 2/2005 | Wu et al. |
| 6,926,815 | B2 * | 8/2005 | Liu .................. G01N 27/44747 204/455 |
| 7,118,675 | B2 | 10/2006 | Siwak et al. |
| 7,118,678 | B2 | 10/2006 | Porat |
| 7,132,049 | B2 | 11/2006 | Hou et al. |
| 7,427,659 | B2 | 9/2008 | Shukla et al. |
| 7,465,397 | B2 | 12/2008 | Siwak et al. |
| 7,714,112 | B2 | 5/2010 | Engstrand et al. |
| 7,951,885 | B2 | 5/2011 | Joehnck et al. |
| 8,067,182 | B2 | 11/2011 | Kelley et al. |
| 8,132,676 | B2 | 3/2012 | Peters et al. |
| 8,765,897 | B2 | 7/2014 | Joehnck et al. |
| 2003/0113603 | A1 | 6/2003 | Highgate |
| 2003/0146156 | A1 | 8/2003 | Siwak et al. |
| 2003/0226799 | A1 | 12/2003 | Charkoudian |
| 2004/0203149 | A1 | 10/2004 | Childs et al. |
| 2005/0107488 | A1 | 5/2005 | Yandrasits et al. |
| 2005/0107594 | A1 | 5/2005 | Sun et al. |
| 2005/0118479 | A1 | 6/2005 | Yamaguchi et al. |
| 2005/0245729 | A1 | 11/2005 | Noel |
| 2008/0119930 | A1 | 5/2008 | Osada et al. |
| 2008/0216942 | A1 | 9/2008 | Hiraoka et al. |
| 2008/0257814 | A1 | 10/2008 | Vigna et al. |
| 2009/0029438 | A1 | 1/2009 | Childs et al. |
| 2009/0208784 | A1 | 8/2009 | Perry et al. |
| 2010/0003328 | A1 | 1/2010 | Yasude et al. |
| 2010/0181254 | A1 | 7/2010 | Graalfs |
| 2010/0288690 | A1 | 11/2010 | Rautio et al. |
| 2010/0311952 | A1 | 12/2010 | Falkenstein et al. |
| 2011/0073547 | A1 | 3/2011 | Joehnck |
| 2011/0136925 | A1 | 6/2011 | Graalfs et al. |
| 2011/0301333 | A1 | 12/2011 | Potty et al. |
| 2012/0029176 | A1 | 2/2012 | Yavorsky et al. |
| 2012/0264920 | A1 | 10/2012 | Wang et al. |
| 2013/0056415 | A1 | 3/2013 | Kozlov et al. |
| 2013/0225701 | A1 | 8/2013 | Soice et al. |
| 2013/0245139 | A1 * | 9/2013 | Kozlov .................. C07K 1/22 521/27 |
| 2014/0301977 | A1 | 10/2014 | Nadarajah et al. |
| 2016/0051943 | A1 | 2/2016 | Kozlov et al. |

FOREIGN PATENT DOCUMENTS

| | | |
|---|---|---|
| CN | 103382215 A | 11/2013 |
| DE | 10-2006-061327 A1 | 6/2008 |
| EP | 0382214 A1 | 8/1990 |
| EP | 1098382 A2 | 5/2001 |
| EP | 1609522 A2 | 12/2005 |
| EP | 1987892 A1 | 11/2008 |
| EP | 2153877 A1 | 2/2010 |
| JP | 2-211865 A | 8/1990 |
| JP | 2000-1548 A | 1/2000 |
| JP | 2001-176556 A | 6/2001 |
| JP | 2002-293848 A | 10/2002 |
| JP | 2002-543971 A | 12/2002 |
| JP | 2003-523499 A | 8/2003 |
| JP | 2003-532746 A | 11/2003 |
| JP | 2005-82728 A | 3/2005 |
| JP | 2005-528213 A | 9/2005 |
| JP | 2006-519273 A | 8/2006 |
| JP | 2007-308399 A | 11/2007 |
| JP | 2007-532477 A | 11/2007 |
| JP | 2008-296220 A | 12/2008 |
| JP | 2009-84694 A | 4/2009 |
| JP | 2009-127035 A | 6/2009 |
| JP | 2010-528271 A | 8/2010 |
| JP | 2011-149024 A | 8/2011 |
| JP | 2011-529508 A | 12/2011 |
| JP | 5234727 B2 | 7/2013 |
| JP | 2013-532829 A | 8/2013 |
| JP | 2013-189427 A | 9/2013 |
| JP | 2013-535683 A | 9/2013 |
| JP | 2013-539787 A | 10/2013 |
| KR | 10-2013-0105340 A | 9/2013 |
| WO | 00/23580 A1 | 4/2000 |
| WO | 00/42423 A1 | 7/2000 |
| WO | 00/50160 A1 | 8/2000 |
| WO | 00/69549 A1 | 11/2000 |
| WO | 03/103814 A1 | 12/2003 |
| WO | 2004/073843 A1 | 9/2004 |
| WO | 2004/103530 A1 | 12/2004 |
| WO | 2005/042131 A1 | 5/2005 |
| WO | 2005/044856 A2 | 5/2005 |
| WO | 2005/052036 A1 | 6/2005 |
| WO | 2006/013612 A1 | 2/2006 |
| WO | 2006/024497 A1 | 3/2006 |
| WO | 2008/065756 A1 | 6/2008 |
| WO | 2008/085116 A1 | 7/2008 |
| WO | 2008/113460 A1 | 9/2008 |
| WO | 2008/145270 A1 | 12/2008 |
| WO | 2008/145351 A1 | 12/2008 |
| WO | 2010/012358 A1 | 2/2010 |
| WO | 2010/031144 A1 | 3/2010 |
| WO | 2010/066676 A1 | 6/2010 |
| WO | 2010/098867 A1 | 9/2010 |
| WO | 2010/133527 A2 | 11/2010 |
| WO | 2011/017514 A1 | 2/2011 |
| WO | 2012/013682 A2 | 2/2012 |
| WO | 2012/015379 A1 | 2/2012 |
| WO | 2012/015908 A2 | 2/2012 |
| WO | 2012/030512 A1 | 3/2012 |
| WO | 2012/051147 A1 | 4/2012 |
| WO | 2012/078677 A2 | 6/2012 |
| WO | 2012/175156 A1 | 12/2012 |
| WO | 2013/067301 A1 | 5/2013 |
| WO | 2013/096322 A1 | 6/2013 |
| WO | 2013/138098 A1 | 9/2013 |
| WO | WO 2013138098 A1 * | 9/2013 ............... C07K 1/22 |

OTHER PUBLICATIONS

Liu et al., "Recovery and purification process development for monoclonal antibody production," mAbs, vol. 2, Iss. 5, pp. 480-499, Sep./Oct. 2010.

Odian, "Chain Copolymerization," Principles of Polymerization, 4th Edition, John Wiley & Sons, 2004.

Polymer Handbook, 3rd Edition, John Wiley & Sons, 1989, part Ii, pp. 181 & 309.

Shukla et al., "Downstream processing of monoclonal antibodies-Application of platform approaches," Journal of Chromatography B, 848 (2007) pp. 28-39.

Stein et al., "Cation exchange chromatography in antibody purification: pH screening for optimised binding and HCP removal," Journal of Chromatography B, 848 (2007) pp. 151-158.

Ulbricht, "Advanced functional polymer membranes," Polymer, 47 (2006) pp. 2217-2262.

European communication dated Jun. 28, 2017 in corresponding European patent application No. 14869655.2.

Gitli et al., "Bicontinuous Hydrogel-Hydrophobic Polymer Systems Through Emulsion Templated Simultaneous Polymerizations," Soft Matter, vol. 4, No. 12, pp. 2475-2485, Sep. 12, 2008.

Liu et al., "Preparation of Polymer-Supported Zirconocene Catalysts and Olefin Polymerization," Journal of Applied Polymer Science, vol. 71, No. 13, pp. 2253-2258, Feb. 3, 1999.

Santa Maria et al., "Synthesis of Crosslinked Resin Based on Methacrylamide, Styrene and Divinylbenzene Dbtained from

(56) References Cited

OTHER PUBLICATIONS

Polymerization in Aqueous Suspension," European Polymer Journal, vol. 39, No. 2, pp. 291-296, Feb. 1, 2003.
Korean communication, with English translation, dated Aug. 1, 2017 in corresponding Korean patent application No. 10-2016-7012481.
Chinese communication, with English translation, dated Aug. 3, 2017 in corresponding Chinese patent application No. 01480067562.6.
Japanese communication, with English translation, dated Jul. 11, 2017 in corresponding Japanese patent application No. 2016-538540.
"Fabrication of Styrene-copolymerized Polyacrylamide Gel," Journal of the Chemical Society of Japan, 1982, No. 3, pp. 414-418.
European communication dated Nov. 28, 2017 in corresponding European patent application No. 14869655.2.
Observation submitted to the Japan Patent Office for the Japanese Patent Application No. 2015-000657, dated May 27, 2016, 10 pages.
International Preliminary Report on Patentability dated Sep. 25, 2014 in co-pending PCT application No. PCT/US2013/028845.
European communication dated Jul. 1, 2013 in co-pending European patent application No. 13275053.0.
European communication dated Oct. 21, 2013 in co-pending European patent application No. 13275053.0.
International Search Report and Written Opinion dated Jun. 21, 2013 in co-pending PCT application No. PCT/US2013/028845.
International Search Report and Written Opinion dated Jul. 8, 2010 in co-pending PCT application No. PCT/US2010/000578.
International Preliminary Report on Patentability dated Sep. 9, 2011 in co-pending PCT application No. PCT/US2010/000578.
Aldington et al., "Scale-Up of Monoclonal Antibody Purification Processes", Journal of Chromatography B, vol. 348, 2007, pp. 64-78.
Anderson et al., "Design of Experiments", Kirk-Othmer Encyclopedia of Chemical Technology, 2010, pp. 1-22.
Bolton et al., "Increasing the Capacity of Parvovirus-Retentive Membranes: Performance of the ViresolveTM Prefilter", Biotechnol. Appl. Biochem. vol. 43, 2006, pp. 55-63.
Brandrup et al., "Free Radical Copolymerization Reactivity Ratios", Polymer Handbook, 3rd Edition, 1989, pp. II/156.
Brooks et al., "Steric Mass-Action Ion Exchange: Displacement Profiles and Induced Salt Gradients", AIChE Journal, Jol. 38, Dec. 1992, pp. 1969-1978.
Fogle et al., "Effects of Resin Ligand Density on Yield and Impurity Clearance in Preparative Cation Exchange chromatography I. Mechanistic Evaluation", Journal of Chromatography A, vol. 1225, 2012, pp. 62-69.
Fouassier, Jean-Pierre, "Photoinitiation, Photopolymerization, and Photocuring", Fundamentals and Applications, Carl Hanser Verlag, Munich, Germany, 1995, pp. 20-93.
Giovannini et al., "Isolation of a Recombinant Antibody from Cell Culture Supernatant: Continuous Annular versus Batch and Expanded-Bed Chromatography", Biotechnology and Bioengineering, vol. 73, No. 6, Jun. 20, 2001, pp. 522-529.
Gueffroy, Donald E., "Buffers: A Guide for the Preparation and use of Buffers in Biological Systems", Calbiochem-Behring Corporation, 1975, 24 pages.

Jungbauer et al., "Comparison of Protein A, Protein G and Copolymerized Hydroxyapatite for the Purification of Human Monoclonal Antibodies", Journal of Chromatography A, vol. 476, 1989, pp. 257-268.
Koros et al., "Terminology for Membranes and Membrane Processes", International Union of Pure and Applied Chemistry (IUPAC). Pure & Appl. Chem., vol. 68, No. 7, 1996, pp. 1479-1489.
Liu et al., "Exploration of Overloaded Cation Exchange Chromatography for Monoclonal Antibody Purification", Journal of Chromatography A, vol. 1218, 2011, pp. 6943-6952.
Pedersen et al., "Whey Proteins as a Model System for Chromatographic Separation of Proteins", Journal of Chromatography B, vol. 790, 2003, pp. 161-173.
Rogers et al., "Development of a Rapid Sanitization Solution for Silica-Based Protein A Affinity Adsorbents", Journal of Chromatography A, vol. 1216, No. 21, May 2009, pp. 4589-4596.
Sakima et al., "Development of a New TOYOPEARL Hydrophobic Interaction Chromatographic Resin for Antibody Purification," TOSOH Research & Technology Review, 2003, vol. 47, pp. 21-27.
Sasagawa et al., "Ionic Crosslinking of SO3H-Group-Containing Graft Chains Helps to Capture Lysozyme in a Permeation Mode", Journal of Chromatography A, vol. 848, Issues 1-2, Jul. 2, 1999, pp. 161-168.
Suda et al., "Comparison of Agarose and Dextran-Grafted Agarose Strong Ion Exchangers for the Separation of Protein Aggregates", Journal of Chromatography A, vol. 1216, 2009, pp. 5256-5264.
Suzuki et al., "Gels of Polyacrylamide Copolymerized with Styrene," Journal of the Chemical Society of Japan, 1982, No. 3, pp. 414-418.
Tang et al., "Novel Cell Sheet Carriers Using PolyIon Complex Gel Modified Membranes for Tissue Engineering Technology for Cell Sheet Manipulation and Transplantation", Reactive & Functional Polymers, Science Direct, vol. 67, 2007, pp. 1388-1397.
Urmann et al., "Influence of Protein and Stationary Phase Properties on Protein-Inatrix-Interaction in Cation Exchange Chromatography", Journal of Chromatography A, vol. 1218, 2011, pp. 5136-5145.
Wu et al., "Effects of Stationary Phase Ligand Density on High-Performance Ion-Exchange Chromatography of Proteins", Journal of Chromatography A, vol. 598, No. 1, May 1, 1992, pp. 7-13.
Office action dated Mar. 26, 2015 in co-pending U.S. Appl. No. 13/783,941.
Office action dated Oct. 1, 2015 in co-pending U.S. Appl. No. 13/783,941.
Final rejection mailed Apr. 29, 2016 in co-pending U.S. Appl. No. 13/783,941.
Office action dated Aug. 17, 2016 in co-pending U.S. Appl. No. 13/783,941.
Final rejection dated Mar. 3, 2017 in co-pending U.S. Appl. No. 13/783,941.
Office action dated Sep. 15, 2017 in co-pending U.S. Appl. No. 13/783,941.
Office action dated Nov. 4, 2014 in co-pending U.S. Appl. No. 13/504,085.
Final rejection dated Apr. 9, 2015 in co-pending U.S. Appl. No. 13/504,085.

* cited by examiner

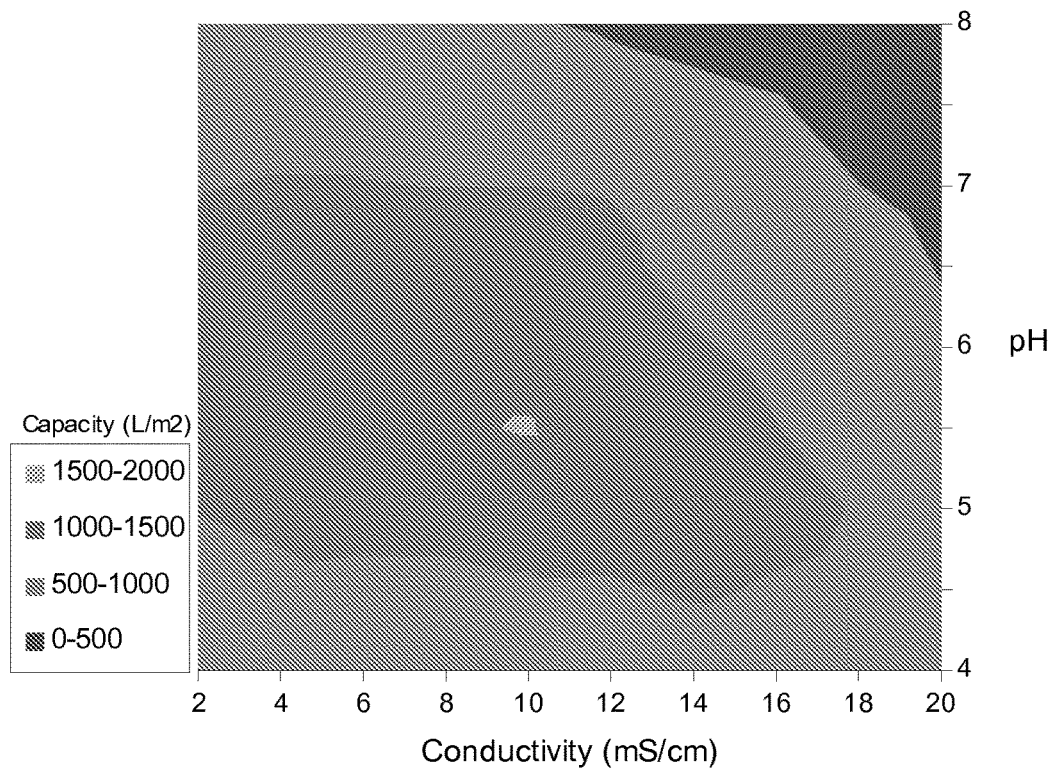
Figure 1. Throughput of a virus filter Viresolve® Pro using a negatively charged prefilter Viresolve® Pro Shield using feed solutions at different pH and conductivity values.

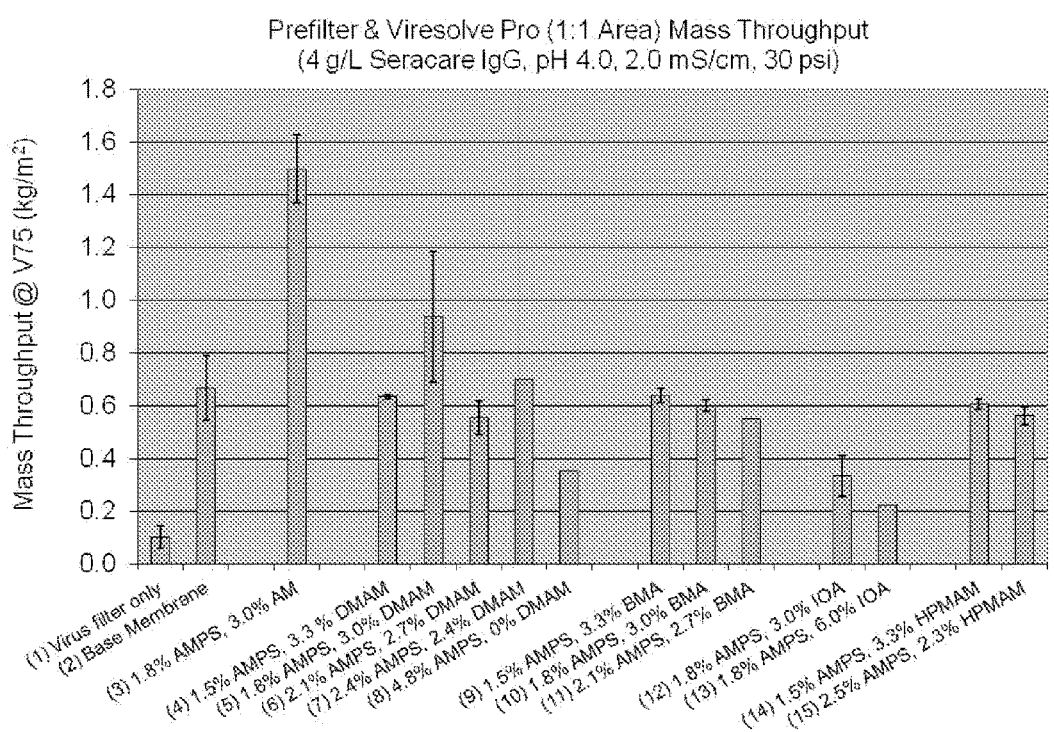
Figure 2. Mass throughputs of Viresolve Pro (VPro) using new adsorptive membranes as prefilters.

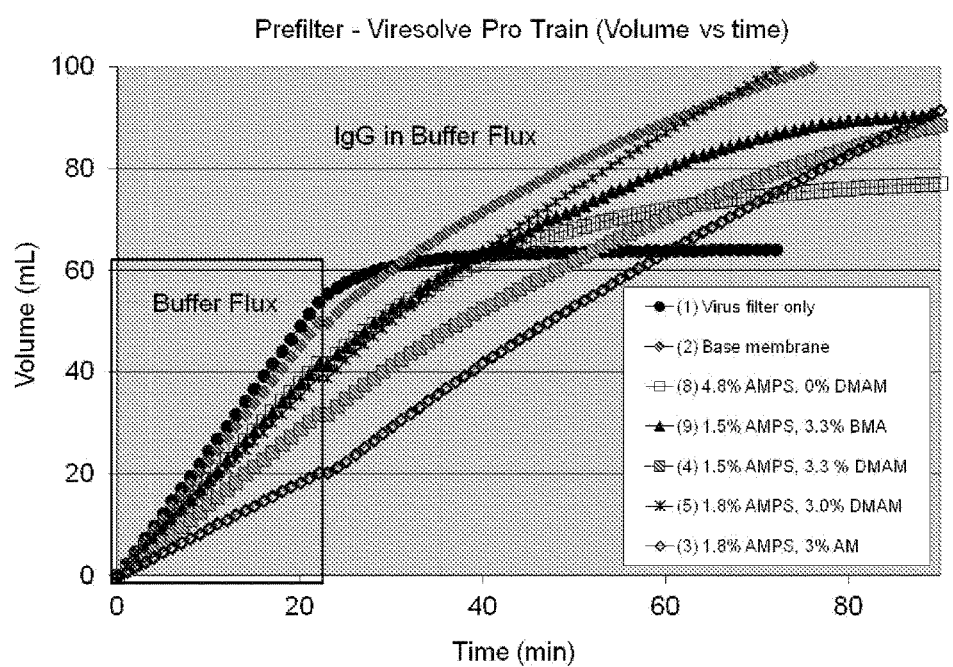
Figure 3. Volume vs. Time curves for buffer and protein solutions for various prefilter/VPro combinations. Slopes of the curves correspond to permeabilities.

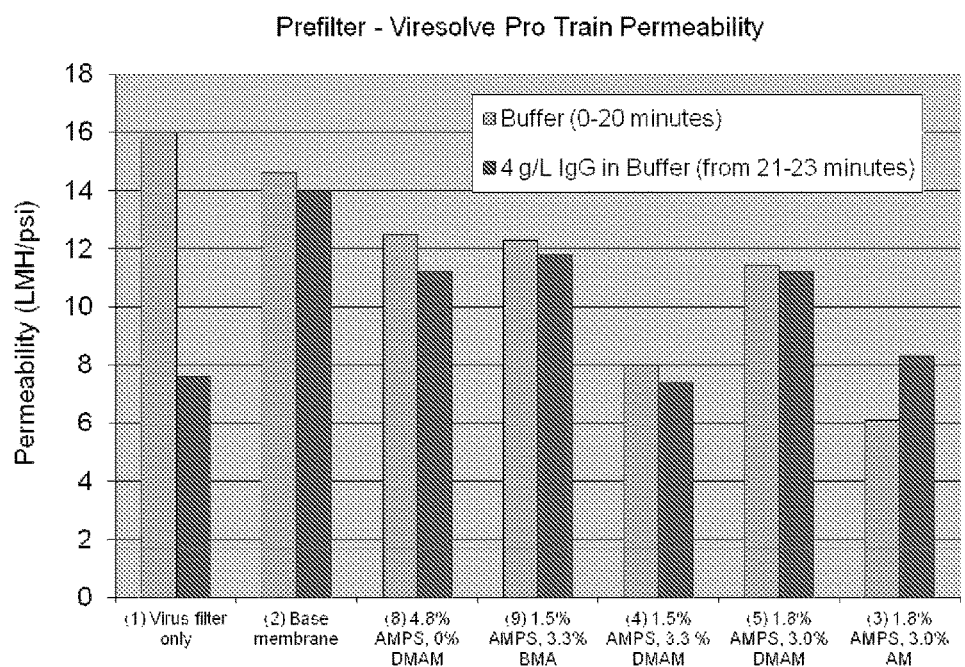
Figure 4. Permeability changes of buffer and protein solution of various prefilter/VPro combinations.

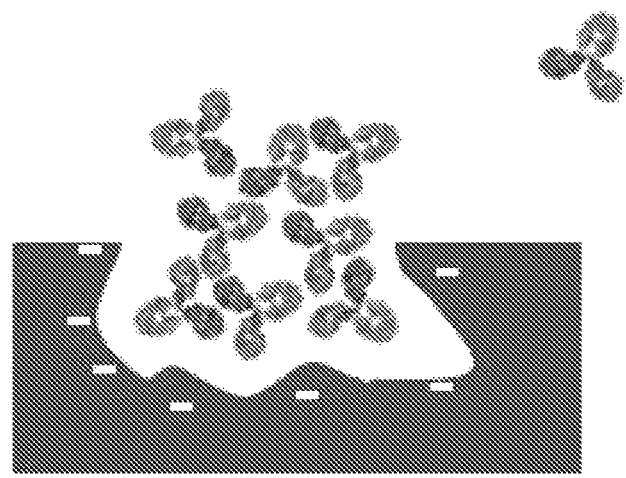
Figure 5. Illustration of a possible mechanism of IgG aggregate interaction with the membrane surface containing Acrylamide.

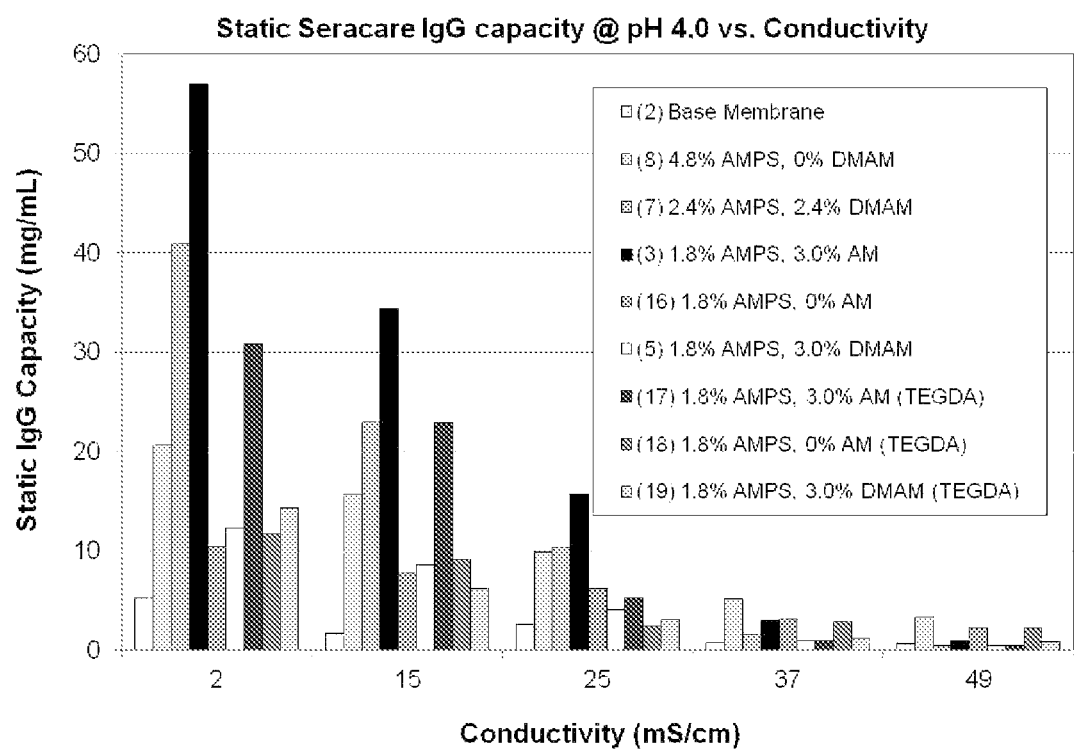
Figure 6. Static binding capacities for IgG of various CEX surface-modified membranes.

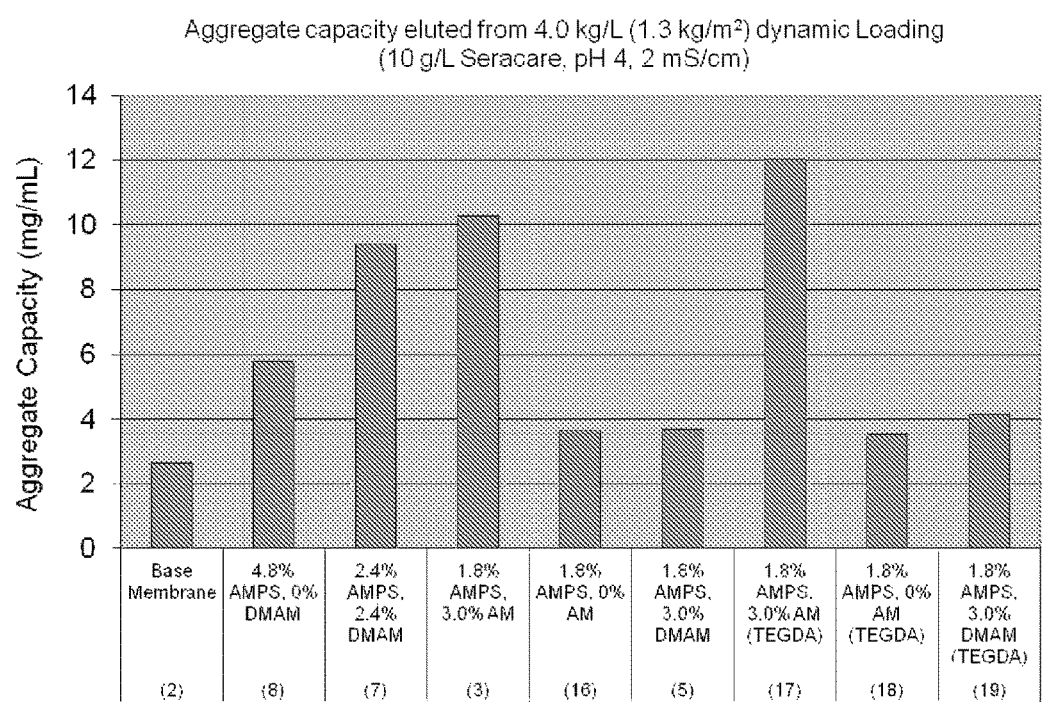
Figure 7. Aggregate binding capacities for IgG of various CEX surface-modified membranes.

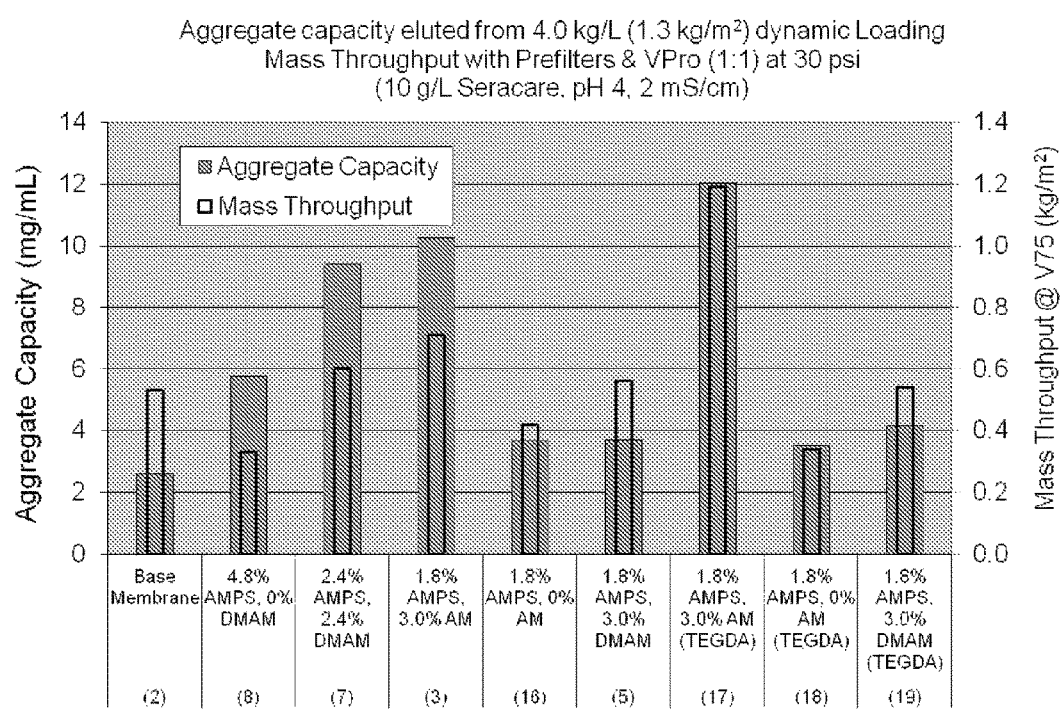
Figure 8. Aggregate binding capacities for IgG of various CEX surface-modified membranes and corresponding VPro throughput.

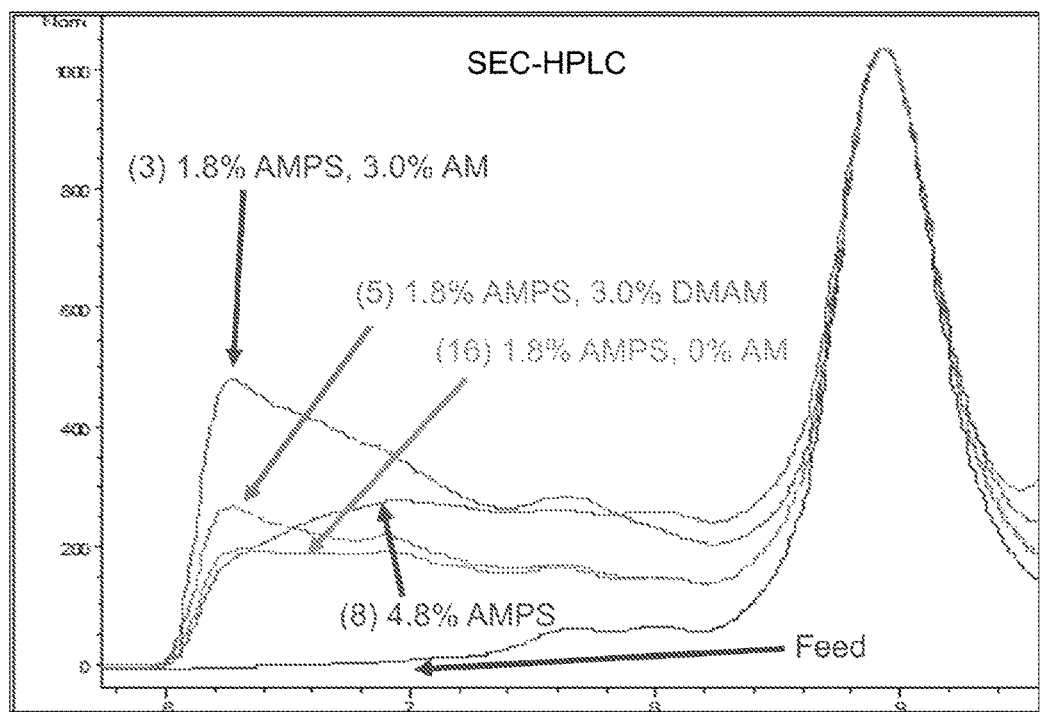
Figure 9. SEC chromatograms of elution IgG samples of various CEX surface-modified membranes.

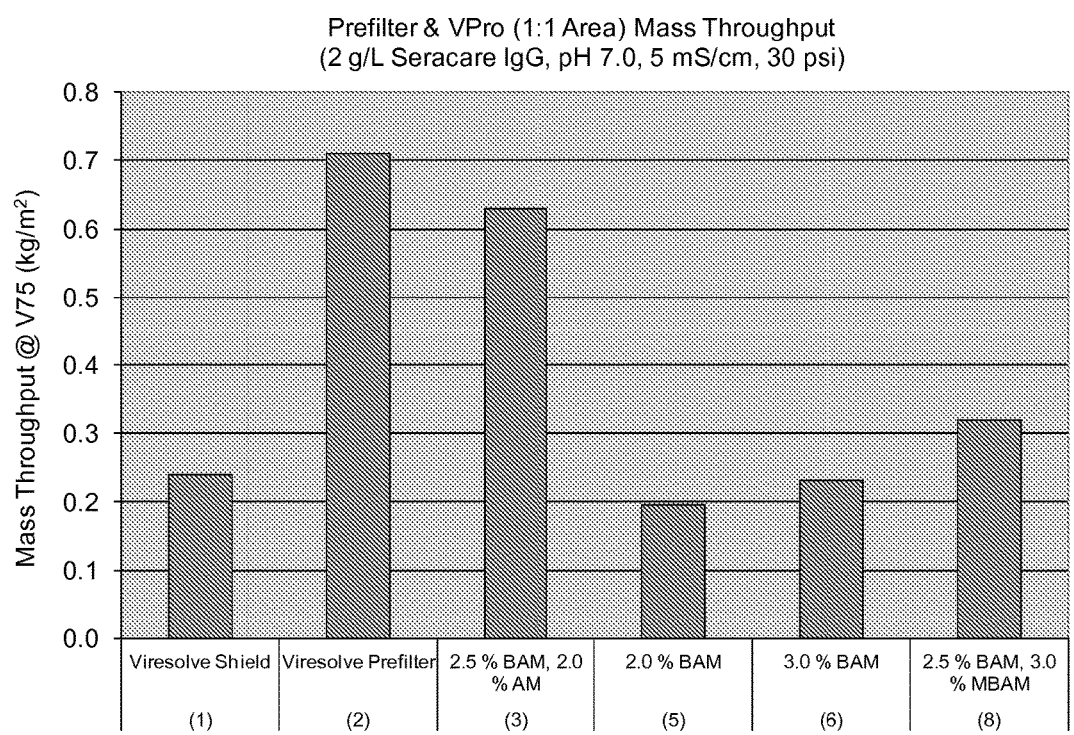
Figure 10. Performance of Acrylamide-containing hydrophobic prefilters in comparison to currently available commercial prefilters and prefilters without Acrylamide at pH 7.0, 5 mS/cm.

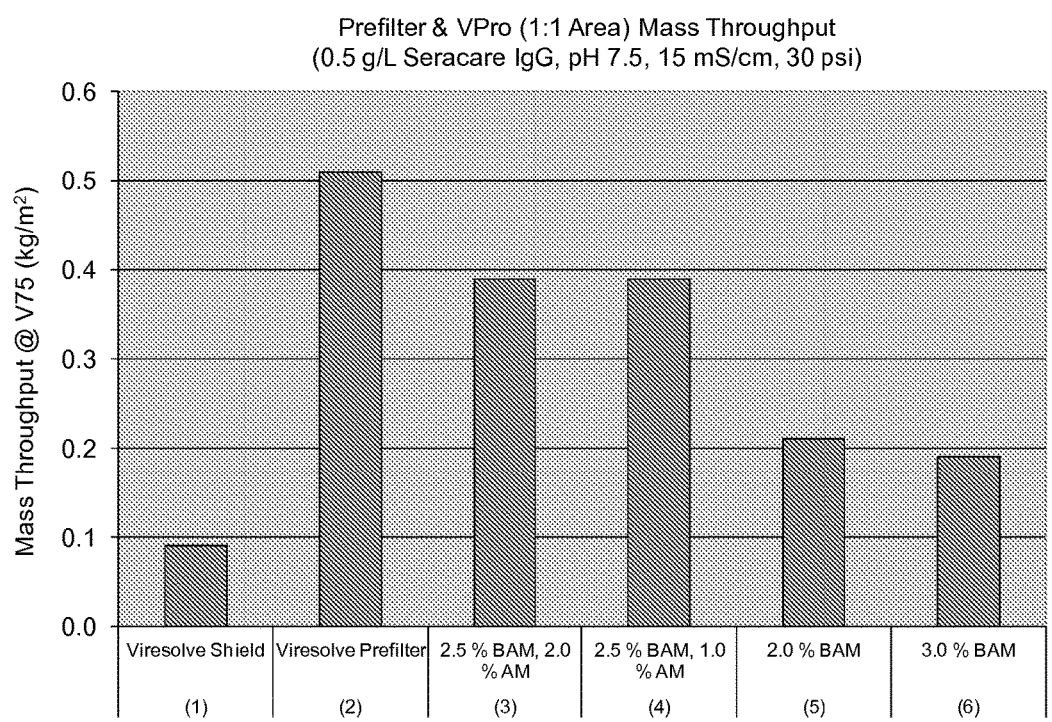
Figure 11. Performance of Acrylamide-containing hydrophobic prefilters in comparison to currently available commercial prefilters and prefilters without Acrylamide at pH 7.5, 15 mS/cm.

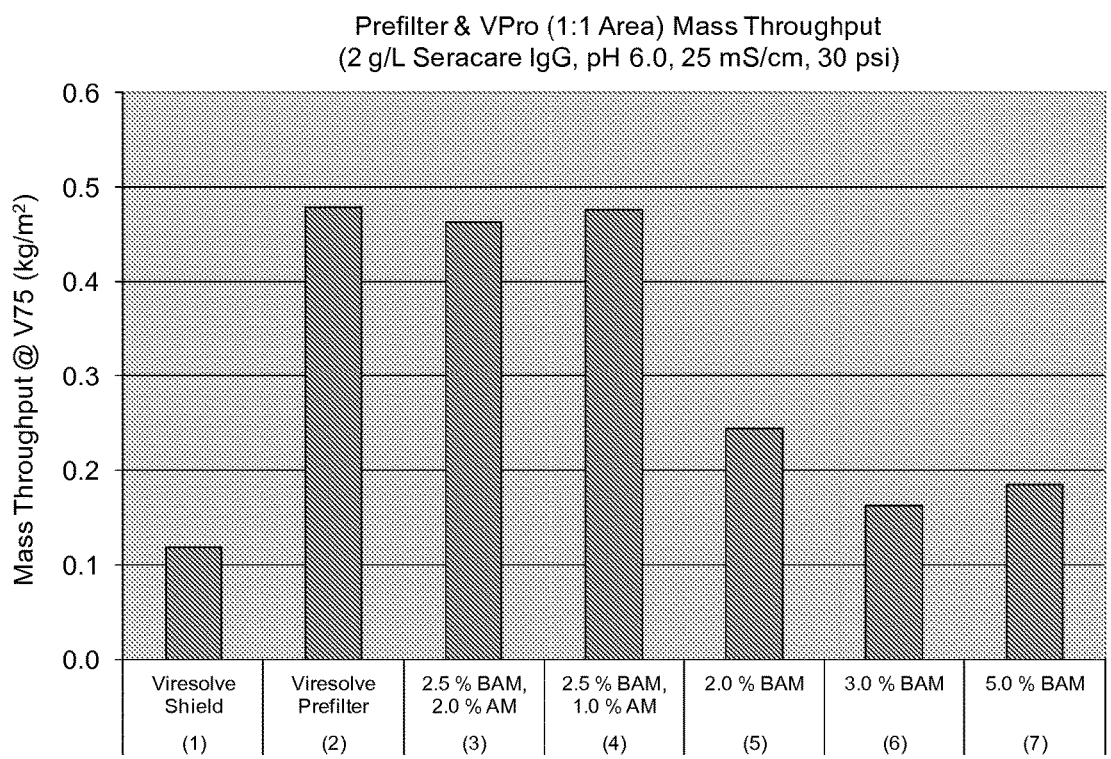
Figure 12. Performance of Acrylamide-containing hydrophobic prefilters in comparison to currently available commercial prefilters and prefilters without Acrylamide at pH 6.0, 25 mS/cm.

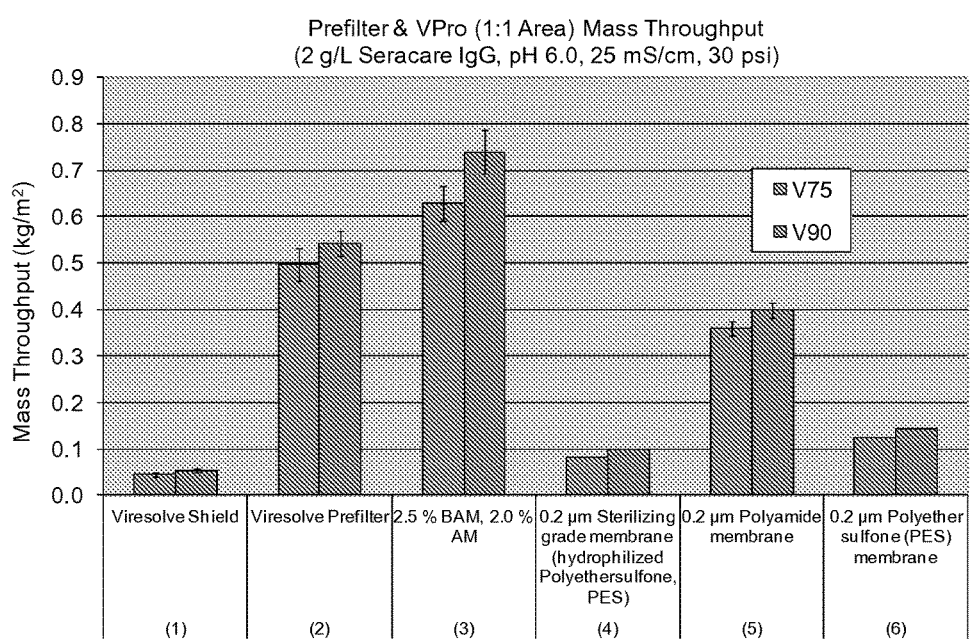
Figure 13. Performance of Acrylamide-containing hydrophobic prefilter in comparison to currently available commercial prefilters and unmodified base membranes at pH 6.0, 25 mS/cm.

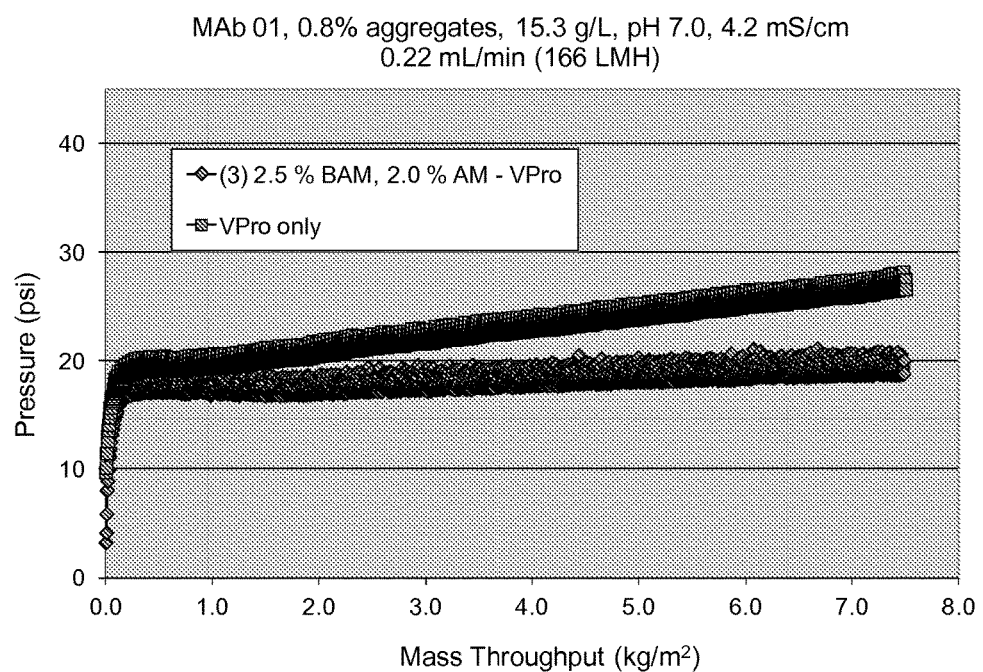
Figure 14. MAb 01 virus filtration performance with membrane (3) and without prefiltration

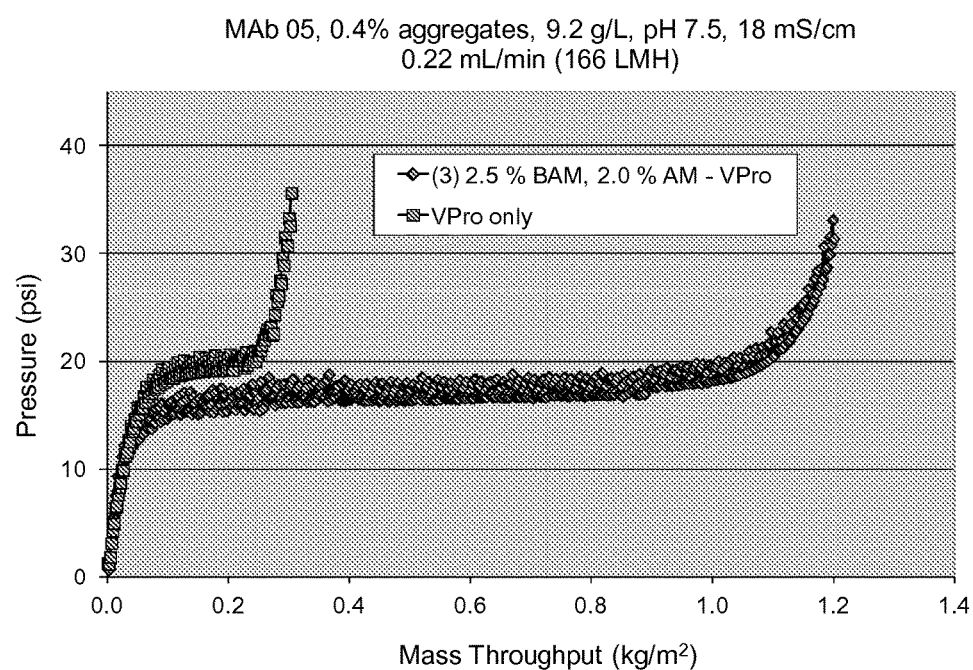
Figure 15. MAb 05 virus filtration performance with membrane (3) and without prefiltration Figure 16. MAb 07 virus filtration performance with membranes (3), (4), (5), and without prefiltration

PROTEIN SEPARATIONS USING AN ACRYLAMIDE CONTAINING FILTER

This application claims priority of U.S. Provisional Application Ser. No. 61/915,125 filed Dec. 12, 2013, the disclosure of which is incorporated herein by reference.

FIELD OF THE INVENTION

Embodiments disclosed herein relate to methods of removing impurities including protein aggregates, from biopharmaceutical preparations containing a product of interest using an acrylamide containing filter.

BACKGROUND

Conventional processes for protein purification typically involve cell culture methods, e.g., using either mammalian or bacterial cell lines recombinantly engineered to produce the protein of interest (e.g., a monoclonal antibody) followed by a cell harvest step to remove cell and cell debris from a cell culture broth. The cell harvest step is usually followed by a capture step, which is typically followed by one or more chromatographic steps, also referred to as polishing steps, which usually include one or more of cation exchange chromatography and/or anion exchange chromatography and/or hydrophobic interaction chromatography and/or mixed mode chromatography and/or hydroxyapatite chromatography. A virus inactivation step may also be included after the capture step. The polishing steps are usually followed by virus filtration and ultrafiltration/diafiltration, which completes the purification process. See, e.g., Shukla et al., J. Chromatography B., 848 (2007) 28-39; Liu et al., MAbs, 2010: September-October 2(5): 480-499.

The virus filtration step is an important step in the purification of proteins, especially when the product is desired to be used in diagnostic or therapeutic applications. The virus filtration step typically employs virus retention filters that retain virus particles while allowing the protein of interest to pass through. One of the challenges with achieving efficient virus filtration is that some of the impurities, especially protein aggregates, have a similar size to the virus particles. Accordingly, protein aggregates end up fouling or plugging the virus retention filter, thereby significantly reducing the flow of the protein of interest through the filter.

Impurities such as protein aggregates form at different stages of the purification process, and in order to maintain adequate throughput of virus retention filters, protein aggregates need to be removed prior to reaching the virus retention filters. Attempts have been made in the prior art to implement flow-through aggregate removal based on Hydrophobic Interactions Chromatography (HIC) media (see, e.g. U.S. Pat. No. 7,427,659). However, HIC-based preparative separations have narrow applicability due to generally difficult process development, narrow operating window, and high concentration of salt required in the buffer.

Weak partitioning chromatography (WPC) is another mode of chromatographic operation, in which the product binds weaker than in the case of bind-elute chromatography but stronger than in the case of flow-through chromatography (See, e.g. U.S. Pat. No. 8,067,182); however, WPC also has certain draw back associated with it including, a narrow operating window and lower binding capacity for impurity removal compared to bind and elute methods.

Further, one of the most convenient ways to selectively remove protein aggregates is by passing a solution of proteins and/or other biomolecules through a filtration media prior to reaching the virus retention filter, whereby the protein aggregates are removed, permitting the protein being purified to flow through onto the viral retention filter. Examples of such filters can be found in U.S. Pat. No. 7,118,675, which discusses filtering a solution of proteins and viruses through an adsorptive depth filter or a charged or surface-modified membrane, prior to the virus filtration step.

Additionally, PCT Publication No. WO2010/098867 discusses using a negatively charged porous medium for removing protein aggregates and PCT Publication No. WO2012/175156 discusses a polyamide-based filter for removing protein aggregates. Lastly, U.S. application Ser. No. 13/783,941, US 20130245139 A1 filed Mar. 4, 2013, discusses use of compositions comprising cation exchange groups for removal of protein aggregates, however, the compositions described therein operate well only under pH and conductivity conditions suitable for cation exchange chromatography.

SUMMARY

Embodiments disclosed herein provide novel compositions for removing impurities such as, protein aggregates, from a sample containing a protein of interest, e.g., an antibody. Accordingly, such compositions can be used prior to the virus filtration step during protein purification, to remove aggregates and protect the virus filter from fouling, therefore improving virus filter capacity.

The compositions described herein provide advantages over the previously known compositions used prior to the virus filtration step to remove impurities such as protein aggregates, in that they can be used under a broad range of solution conditions.

In some embodiments, the compositions are negatively charged. In other embodiments, the compositions are neutral (hydrophobic).

In some embodiments, the compositions can be used under low pH and low conductivity conditions (e.g., negatively charged compositions). In other embodiments, the compositions can be used under neutral to higher pH and moderate to high conductivity conditions (e.g., hydrophobic compositions).

In some embodiments, a flow-through method of separating a monomeric protein of interest from protein aggregates in a sample is provided, where the method comprises contacting the sample with a porous solid support comprising a co-polymer comprising at least two monomers, wherein at least one of the monomers comprises acrylamide and at least a second monomer comprises a hydrophobic binding group, where the solid support selectively binds protein aggregates, thereby to separate the monomeric protein of interest from the protein aggregates; and wherein the method can be performed under conditions conducive for hydrophobic interaction, e.g., neutral to higher pH and moderate to high conductivity conditions.

In some embodiments, a hydrophobic binding group is selected from the group consisting of an ethyl group, a butyl group, a hexyl group, a 2-ethylhexyl group, a dodecyl group, a stearyl group, a hydroxypropyl group, a phenyl group and a benzyl group.

In a particular embodiment, the hydrophobic binding group is benzyl acrylamide.

In some embodiments, a co-polymer according to the compositions described herein comprises the following structure:

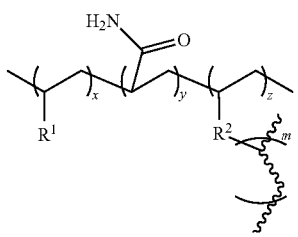

Formula A where x, y and z are average molar fractions of each monomer in the co-polymer and range independently from about 0.01 to 0.99;

$R^1$ is a hydrophobic aliphatic or hydrophobic aromatic binding group selected from the group consisting of an ethyl group, a butyl group, a hexyl group, a 2-ethylhexyl group, a dodecyl group, a stearyl group, a hydroxypropyl group, a phenyl group and a benzyl group;

$R^2$ is an uncharged aliphatic or aromatic organic linker between two polymers derived from a polymerizable monomer selected from the group consisting of acrylates, acrylamides, methacrylates, vinyl ethers and styrenics; and m denotes that a similar co-polymer chain is attached at the other end of the linker.

In some embodiments, a co-polymer according to the compositions described herein comprises the following structure:

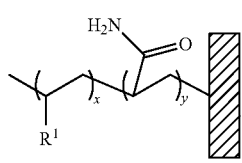

Formula B where x and y are average molar fractions of each monomer in the co-polymer, and range independently from about 0.01 to 0.99; and $R^1$ is a hydrophobic aliphatic or hydrophobic aromatic binding group selected from the group consisting of an ethyl group, a butyl group, a hexyl group, a 2-ethylhexyl group, a dodecyl group, a stearyl group, a hydroxypropyl group, a phenyl group and a benzyl group, where the co-polymer is grafted via covalent linkage onto a solid support, shown as the rectangle.

In various structures described herein, the hydrophobic binding group is a benzyl acrylamide group. In certain embodiments, a filtration train is provided that includes one or more of a prefilter, a clarifying filter, chromatography media (e.g., cation exchange, anion exchange), a membrane adsorber, and a viral clearance filter to remove product/process contaminants.

In certain embodiments, the prefilter comprises a porous solid support comprising a co-polymer comprising at least two monomers, wherein at least one of the monomers comprises acrylamide and at least a second monomer comprises a hydrophobic binding group.

BRIEF DESCRIPTION OF THE DRAWINGS

FIG. 1 depicts a contour graph demonstrating the throughput of a virus filter Viresolve® Pro, when using a negatively charged prefilter upstream of the virus filter with an IgG feed solution at different pH and conductivity values. The X-axis represents conductivity (mS/cm) and the right-hand Y-axis represents pH.

FIG. 2 depicts a bar graph demonstrating the mass throughputs of Viresolve® Pro (VPro) virus filter when using the following prefilters upstream of the virus filter: prefilter containing 1.8% AMPS and 3.0% AM (3); prefilter containing 1.5% AMPS and 3.3% DMAM (4); prefilter containing 1.8% AMPS and 3.0% DMAM (5); prefilter containing 2.1% AMPS and 2.7% DMAM (6); prefilter containing 2.4% AMPS and 2.4% DMAM (7); prefilter containing 4.8% AMPS and 0% DMAM (8); prefilter containing 1.5% AMPS and 3.3% BMA (9); prefilter containing 1.8% AMPS and 3.0% BMA (10); prefilter containing 2.1% AMPS and 2.7% BMA (11); prefilter containing 1.8% AMPS and 3.0% IOA (12); prefilter containing 1.8% AMPS and 6.0% IOA (13); prefilter containing 1.5% AMPS and 3.3% HPMAM (14) and prefilter containing 2.5% AMPS and 2.3% HPMAM (15). The first two bars in the bar graph depict controls: virus filter only (1) and prefilter base membrane without any modifications (2). The X-axis represents the prefilter compositions and the Y-axis represents mass throughput in kg of IgG/m2 of virus membrane filter at V75. Prefilter to virus filter area is 1:1 at 3.1 cm2.

FIG. 3 depicts a graph demonstrating the Volume vs. Time curves for buffer and protein solutions for various prefilter/virus filter combinations (Table 2). Slopes of the curves correspond to permeabilities. The X-axis represents time (min) and the Y-axis represents volume (mL). Prefilter containing 1.8% AMPS and 3.0% AM (3) is the only train to show an increase in permeability in the presence of IgG in the same buffer used for the initial flux.

FIG. 4 depicts a bar graph representing the permeability changes (y-axis in LMH/psi) of the filtration trains of the various prefilter/virus filter combinations, x-axis (Table 2) as they are switched from buffer only to IgG solutions in the same buffer. The train containing Prefilter (3) containing 1.8% AMPS and 3.0% AM is the only train to show an increase in permeability in the presence of IgG.

FIG. 5 depicts an illustration of the possible mechanism for the permeability increase observed in FIGS. 3 and 4 with the membrane surface containing Acrylamide (Prefilter 3). The increase in permeability of the Prefilter 3/VPro combination (Table 2) is resultant of the unique negatively charged hydrogel surface containing acrylamide contracting from ionic interactions with the positively charged IgG.

FIG. 6 depicts Static binding capacities for IgG (y-axis in mg of IgG/mL of membrane) of various CEX surface-modified membranes in Table 3 at pH 4.0 and at different solution conductivities (y-axis, mS/cm). The presence of the small, neutral, and hydrophilic acrylamide with the CEX binding group AMPS in membranes 3 and 17 allows for a unique polymer hydrogel which provides greater static IgG capacities at conductivities ≤25 mS/cm.

FIG. 7 depicts Aggregate binding capacities (y-axis, mg/mL) for IgG of the various CEX surface-modified membranes (x-axis) in Table 3 after equivalent dynamic loadings under CEX binding conditions to membranes. The CEX elutions after equivalent loading are used to determine the IgG capacity, aggregate selectivity by analytical size exclusion chromatography (SEC), and to calculate aggregate capacity of the membranes in Table 4. The dynamic CEX aggregate capacity is measured for the membranes in Table 3 to quantify the aggregate selectivity differences of the membranes in Table 3.

FIG. 8 shows that membranes with higher aggregate capacities (Table 4, FIG. 7) tend to provide better virus filter (Viresolve® Pro) protection, thereby yielding higher IgG mass throughputs (right Y-axis) using the process in Example 1.

FIG. 9 is a representative chromatogram of a normalized SEC-HPLC overlay (y-axis is UV230 nm Abs and x-axis is minutes) including the feed loading solution and elutions from membranes 3, 16, 5, and 8 from Table 4. The overlay shows that the elution off of membrane 3 that contains acrylamide has a higher percentage of aggregates than membranes 8 and 16 without a neutral co-monomer, or membrane 5 with the co-monomer DMAM. This result demonstrates that the presence of acrylamide improves the membrane selectivity for aggregates (Greater peak area from 6-8.5 minutes).

FIGS. 10, 11, and 12 show membranes 3 and 4 (Table 5) modified with 2.5% BAM, 1.0 or 2.0% acrylamide provide greater protection (kg/m2, y-axis) of the virus removal filter (greater mass throughput at pH 7.0 and 5 mS/cm, pH 7.5 and 15 mS/cm, and pH 6.0 and 25 mS/cm) than membranes 5, 6, 7, or 8 (Table 5, x-axis) which did not contain acrylamide. The acrylamide-containing membranes 3 and 4 also provide similar mass throughput to the virus prefilter (Viresolve® Prefilter) (primarily hydrophobic mechanism) and much better throughput than the Viresolve® Shield (CEX mechanism) under the 3 solution conditions.

FIG. 13 shows membrane (3) (Table 5 and 6) provides greater protection (kg/m2, y-axis) of the virus removal filter at pH 6.0 and 25 mS/cm than commercially available prefilters and unmodified membranes from Table 6.

FIG. 14 (Table 7) shows membrane (3) is effective at reducing the pressure increase (y-axis) compared to non-prefiltered VPro to reduce fouling and provide greater mass throughput (x-axis) of VPro for MAb01 at pH 7.0, 4.2 mS/cm, 15.3 g/L, at 0.22 mL/min (166 LMH), containing 0.8% aggregates by SEC-HPLC.

FIG. 15 (Table 7) shows membrane (3) protects VPro to improve mass throughput (x-axis) 4× of MAb 05 by reducing pressure (y-axis) which is indicative of fouling compared to non-prefiltered VPro for MAb05 at pH 7.5, 18 mS/cm, 9.2 g/L, at 0.22 mL/min (166 LMH), containing 0.4% aggregates by SEC-HPLC.

FIG. 16 (Table 7) shows membrane (3) protects VPro to improve mass throughput (x-axis, kg/m2) by reducing pressure increase (y-axis) which is indicative of fouling better than VPro virus filtration without prefiltration, and with unmodified membrane prefilters composed of polyamide (5), and the commercial sterilizing grade membrane filter (4) for MAb07 at pH 7.0, 8 mS/cm, 8 g/L, at 0.22 mL/min (166 LMH), containing 4% aggregates by SEC-HPLC.

DETAILED DESCRIPTION

In order that the embodiments disclosed herein may be more readily understood, certain terms are first defined. Additional definitions are set forth throughout the detailed description.

I. Definitions

The term "chromatography," as used herein, refers to any kind of technique which separates the product of interest (e.g., a therapeutic protein or antibody) from contaminants and/or protein aggregates in a biopharmaceutical preparation.

The terms "flow-through process," "flow-through mode," and "flow-through chromatography," as used interchangeably herein, refer to a product separation technique in which a biopharmaceutical preparation containing the product of interest is intended to flow-through a material. In some embodiments, the product of interest flows through the material and the undesirable entities bind to the material. In various embodiments described herein, the product of interest flows through a material containing acrylamide. In a particular embodiment, the material contains a co-polymer comprising acrylamide, where the material is used prior to the virus filtration step in a protein purification process, i.e., as a virus-filter The terms "contaminant," "impurity," and "debris," as used interchangeably herein, refer to any foreign or objectionable molecule, including a biological macromolecule such as a DNA, an RNA, one or more host cell proteins, endotoxins, lipids, protein aggregates and one or more additives which may be present in a sample containing the product of interest that is being separated from one or more of the foreign or objectionable molecules. Additionally, such a contaminant may include any reagent which is used in a step which may occur prior to the separation process. In a particular embodiment, compositions and methods described herein are intended to selectively remove protein aggregates, from a sample containing a product of interest. In some embodiments, the compositions and methods described herein are used prior to a virus filtration step, thereby removing protein aggregates and other impurities that foul the virus retention filter and adversely affect the permeability of the protein of interest through the filter.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The term "antigen-binding fragment" refers to a polypeptide portion of an immunoglobulin or antibody that binds an antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', F(ab')2, Fv, single chains, and single-chain antibodies.

As used herein, the term "sample" refers to any composition or mixture that contains a target protein to be purified. Samples may be derived from biological or other sources. Biological sources include eukaryotic and prokaryotic sources, such as plant and animal cells, tissues and organs. In some embodiments, a sample includes a biopharmaceutical preparation containing a protein of interest to be purified. In a particular embodiment, the sample is a cell culture feed containing a protein of interest to be purified. The sample may also include diluents, buffers, detergents, and contaminating species, debris and the like that are found mixed with the target protein or protein of interest. The sample may be "partially purified" (i.e., having been subjected to one or more purification steps, such as filtration steps) or may be obtained directly from a host cell or organism producing the target molecule (e.g., the sample may comprise harvested cell culture fluid). In some embodiments, a sample which is subjected to the flow-through purification processes described herein is an eluate from a bind and elute chromatography step, e.g., a Protein A affinity chromatography.

The term "virus membrane plugging species" or "virus membrane plugging impurities" may refer to any soluble or solubilized components of solution that contribute significantly to pore blocking or fouling of a porous membrane designed to retain viral particles, i.e., a virus filtration membrane or a virus retention membrane. In general, the size of these species will be larger than the protein of interest and in some instances may be comparable to the size of viral particles that are intended to be retained by the virus membrane.

In various embodiments, compositions provided herein are meant to capture such virus membrane plugging species, and are used prior to a virus retention membrane during a protein purification process. In various embodiments, the virus membrane plugging species include protein aggregates.

The term "protein aggregate" or "protein aggregates," as used interchangeably herein, refers to an association of at least two molecules of a product of interest, e.g., a therapeutic protein or antibody. The association of at least two molecules of a product of interest may arise by any means including, but not limited to, covalent, non-covalent, disulfide, or nonreducible crosslinking.

Aggregate concentration can be measured in a protein sample using Size Exclusion Chromatography (SEC), a well known and widely accepted method in the art (see, e.g., Gabrielson et al., *J. Pharm. Sci.*, 96, (2007), 268-279). Relative concentrations of species of various molecular weights are measured in the effluent using UV absorbance, while the molecular weights of the fractions are determined by performing system calibration following instruction of column manufacturer.

The term "dimer," "dimers," "protein dimer" or "protein dimers," as used interchangeably herein, refers to a lower order fraction of protein aggregates, which is predominantly comprised of aggregates containing two monomeric molecules, but may also contain some amount of trimers and tetramers. This fraction is usually observed as the first resolvable peak in a SEC chromatogram immediately prior to the main monomer peak.

The term "high molecular weight aggregates," or "HMW," as used interchangeably herein, refers to a higher order fraction of protein aggregates, i.e. pentamers and above. This fraction is usually observed as one or more peaks in a SEC chromatogram prior to the dimer peak.

The term "solid support," as used herein, refers in general to any material (porous or non porous) which includes a co-polymer comprising acrylamide and a hydrophobic binding group. Examples of solid support formats used in the methods and compositions described herein include, but are not limited to, membranes, porous beads, winged fibers, monoliths, chromatographic resins, woven fabrics and nonwoven fabrics.

The term "selectivity," as used herein, refers to the dimensionless ratio of partition coefficients of two species between a mobile phase and a stationary phase. A partition coefficient ($K_p$) is the ratio Q/C, where Q and C are the bound and free protein concentrations, respectively.

The term "hydrophobic binding group," as used herein, refers to a non-polar aliphatic or aromatic organic "hydrophobic" residue capable of intermolecular association with another hydrophobic surface, which is defined as a hydrophobic interaction. Exemplary hydrophobic groups are alkyl, cycloalkyl, haloalkyl, fluoroalkyl, aryl, and the like. In a particular embodiment, a hydrophobic binding group is benzylacrylamide.

The term "neutral to higher pH" refers to a pH of 6 or greater on the scale of 0-14 determined from the equilibrium of the ions in water being $[H_3O^+][OH^-]=1.0\times10^{-14}$ where pH=−log $[H_3O^+]$.

The term "moderate to high conductivity" refers to a solution condition where the ionic conductivity measured in milliSiemens/centimeter is equal to or typically greater than 5 mS/cm. The solution conductivity is the electrical conductivity of a solution with electrolytes is measured by determining the resistance of the solution between two flat or cylindrical electrodes separated by a fixed distance.

The term "viral prefilter" or "prefilter" refers to a normal flow filtration media, membrane, or device used upstream of a virus filter or viral retention filter and which is used to improve the throughput of the virus filter by removing impurities that prematurely plug the virus filter such as, e.g., protein aggregates.

The term "virus filter" or "viral retention filter" refers to a membrane or media that retains viruses or viral particles on the order of 20-100 nm by a size-exclusion mechanism, to provide viral clearance during a protein purification process. Examples of virus retention filters include Viresolve® Pro, Viresolve® NFP and Virosolve® NFR.

II. Exemplary Solid Supports

Embodiments disclosed herein provide solid supports comprising a co-polymer, where at least one of the monomers is acrylamide. The solid supports described herein bind virus filter plugging species or impurities such as, protein aggregates, more favorably than the monomeric form of a protein which is usually the product of interest. Without wishing to be bound by theory, it is contemplated that any suitable solid support format may be used. For example, the solid support can be porous or non-porous or it can be continuous, such as in the form of a monolith or membrane. The solid support could also be discontinuous, such as in the form of particles, beads, or fibers. In either case (continuous or discontinuous), the important features of the solid support are that they have a high surface area, mechanical integrity, integrity in aqueous environment, and ability to provide flow distribution to ensure accessibility of the binding groups.

Exemplary continuous porous solid supports include microporous membranes, i.e. having a pore sizes between about 0.05 micron and 10 micron. Porous membranes that may be used in the compositions and methods according to the embodiments disclosed herein may be classified as symmetric or asymmetric in nature, which refers to the uniformity of the pore sizes across the thickness of the membrane, or, for a hollow fiber, across the microporous wall of the fiber. As used herein, the term "symmetric membrane" refers to a membrane that has substantially uniform pore size across the membrane cross-section. As used herein, the term "asymmetric membrane" refers to a membrane in which the average pore size is not constant across the membrane cross-section. In some embodiments, in case of asymmetric membranes, pore sizes can vary evenly or discontinuously as a function of location throughout the membrane cross-section. In some embodiments, asymmetric membranes can have a ratio of pore sizes on one external surface to pore sizes on the opposite external surface, which ratio is substantially greater than one.

A wide variety of microporous membranes made from a wide variety of materials may be used in the compositions and methods described herein. Examples of such materials include polysaccharides, synthetic and semi-synthetic polymers, metals, metal oxides, ceramics, glass, and combinations thereof.

Exemplary polymers that can be used to manufacture the microporous membranes that may be used in the compositions and methods described herein include, but are not limited to, substituted or unsubstituted polyacrylamides, polystyrenes, polymethacrylamides, polyimides, polyacrylates, polycarbonates, polymethacrylates, polyvinyl hydrophilic polymers, polystyrenes, polysulfones, polyethersulfones, copolymers or styrene and divinylbenzene, aromatic polysulfones, polytetrafluoroethylenes (PTFE), perfluorinated thermoplastic polymers, polyolefins, aromatic polyamides, aliphatic polyamides, ultrahigh molecular weight polyethylenes, polyvinylidene difluoride (PVDF), polyetheretherketones (PEEK), polyesters, and combinations thereof.

Exemplary commercially available microporous membranes are Durapore® and Millipore Express® available from EMD Millipore Corp. (Billerica, Mass.); Supor® available from Pall Corp. (Port Washington, N.Y.); and Sartopore® and Sartobran® available from Sartorius Stedim Biotech S.A. (Aubagne Cedex, France).

Other exemplary continuous solid supports are monoliths, such as CIM® monolithic materials available from BIA Separations (Villach, Austria).

Exemplary discontinuous solid supports include porous chromatography beads. As will be readily recognized by those skilled in the art, chromatography beads can be manufactured from a great variety of polymeric and inorganic materials, such polysaccharides, acrylates, methacrylates, polystyrenics, vinyl ethers, controlled pore glass, ceramics and the like.

Exemplary commercially available chromatography beads are CPG from EMD Millipore Corp.; Sepharose® from GE Healthcare Life Sciences AB; TOYOPEARL® from Tosoh Bioscience; and POROS® from Life Technologies.

Other exemplary solid supports are woven and non-woven fibrous materials, such as fiber mats and felts, as well as fibers packed into a suitable housing, for example chromatography column, disposable plastic housing, and the like. Exemplary Solid supports also include winged fibers.

III. Exemplary Binding Groups

In various embodiments described herein, compositions comprise a co-polymer of acrylamide and a binding group.

A great variety of binding groups or ligands can be attached to solid supports and used for effective removal of protein aggregates from a sample, as described herein. In general, the binding group should be capable of attracting and binding to protein aggregates in a solution. Protein attraction to the binding group can be of any type, including ionic (e.g., cationic exchange groups), polar, dispersive, hydrophobic, affinity, metal chelating, or van der Waals.

Exemplary ionic binding groups include, but are not limited to, sulfate, sulfonate, phosphate, phosphonate, carboxylate; primary, secondary, tertiary amine and quaternary ammonium; heterocyclic amines, such as pyridine, pyrimidine, pyridinium, piperazine, and the like.

Polar groups include a wide variety of chemical entities comprising polarized chemical bonds, such C—O, C═O, C—N, C═N, C≡N, N—H, O—H, C—F, C—Cl, C—Br, C—S, S—H, S—O, S═O, C—P, P—O, P═O, P—H. Exemplary polar groups are carbonyl, carboxyl, alcohol, thiol, amide, halide, amine, ester, ether, thioester, and the like.

In some embodiments described herein, compositions described herein include a co-polymer of acrylamide and a hydrophobic binding group. Hydrophobic binding groups are capable of hydrophobic interactions. Exemplary hydrophobic groups are alkyl, cycloalkyl, haloalkyl, fluoroalkyl, aryl, and the like. Exemplary aryl groups are benzyl, phenyl, naphthyl, tolyl, and the like.

Affinity binding groups are arrangements of several binding functionalities that in concert provide a highly specific interaction with target protein. Exemplary affinity binding groups include Protein A and Protein G and domains and variants thereof.

In some embodiments, a binding group is an ionic group. In a particular embodiment, a binding group is a negatively charged sulfonate group. In general, negatively charged sulfonate groups have several advantages. For example, they exhibit broad applicability to bind positively charged proteins in solution; the chemistry is inexpensive and straightforward with many synthetic manufacturing methods readily available; the interaction between the binding group and proteins is well understood (See, e.g., Stein et al., *J. Chrom. B*, 848 (2007) 151-158), and the interaction can be easily manipulated by altering solution conditions, and such interaction can be isolated from other interactions.

In some embodiments, a preferred binding group is a hydrophobic group. Hydrophobic binding groups offer advantages of binding solution species under the conditions of higher ionic conductivity, where ionic binding groups are less effective. In a particular embodiment, a binding group is an aromatic hydrocarbon group, for example, benzyl group, or alternatively an ethyl group, a butyl group, a hexyl group, a 2-ethylhexyl group, a dodecyl group, a stearyl group, a hydroxypropyl group, or a phenyl group.

In addition to binding groups, the solid support may also contain neutral groups (e.g., acrylamide) that are present together with binding groups and serve any one or more of the following: separating binding groups to an optimum distance between one another, providing water wettability to the porous support, reducing non-specific interactions between the sample and the solid support, controlling water absorption and swelling of the polymeric structure containing binding groups, providing suitable mechanical properties to the polymeric structure containing binding groups, improving adhesion of the polymeric structure to the solid support, providing secondary interactions with the sample that increase capacity and/or selectivity.

Exemplary neutral groups are alcohols, sugars, glycols, ethers, amides, nitriles and the like. A preferred neutral group is a simple amide group, $C(=O)-NH_2$.

IV. Methods of Attaching the Binding Groups to a Solid Support

In the compositions and methods described herein, suitable binding groups (e.g., ionic or hydrophobic binding groups) are attached to a solid support, to provide a greater capacity to bind protein aggregates versus the product of interest.

The compositions and methods described herein are based on a surprising and unexpected discovery that presence of acrylamide in the composition significantly enhances the selectivity of solid supports for virus membrane plugging species, including larger order protein aggregates.

The compositions and methods described herein are especially effective in the removal of lower order protein aggregates such as, e.g., dimers, trimers and tetramers, in a flow-through mode, which are generally more difficult to separate from the monomeric form of proteins, as compared to higher order aggregates such as, e.g., pentamers and higher.

A variety of methods known in the art and those described herein can be used for attaching binding groups to a solid support for use in the methods described herein. In general, the criteria of successful attachment include achievement of the desired binding group density and low rate of detachment of binding groups (i.e., low leaching of binding groups). The binding groups could be attached directly to a solid support, or could be incorporated into a polymeric molecule, which, in turn, can be attached to a solid support. Alternatively, the binding groups can be incorporated into a cross-linked coating applied onto a solid support, with or without forming a chemical bond between the coating and the solid support.

A number of methods are known in the art for attaching the binding groups to a solid support (see, for example, Ulbricht, M., Advanced Functional Polymer Membranes, *Polymer*, 47, 2006, 2217-2262). These methods include, but are not limited to, direct modification of the solid support with binding groups through suitable coupling chemistry; adsorbing, and attaching polymeric molecules. The latter can be accomplished by either grafting "to" (when the polymer is pre-made before reaction with the surface) or grafting "from" (when the polymerization is initiated using the surface groups).

The choice of monomers used in creating a polymer comprising binding groups is dictated by reactivity of the monomers. Reactivities of various monomer types and the effects on the polymer composition are well studied and documented (see, for example, *Polymer Handbook*, 3' ed., John Wiley & Sons, 1989, p. II). Well-accepted parameters of monomers that predict the composition of the polymer and its structure are the reactivity ratios of the monomers (see, for example, Odian, J., *Principles of Polymerization*, 4th ed., John Wiley & Sons, 2004, p. 466).

A preferred method to attach the ionic or hydrophobic binding groups to the solid support is an in situ polymerization reaction that incorporates the binding group into a cross-linked coating applied onto the solid support. This method is disclosed in U.S. Pat. Nos. 4,944,879 and 4,618,533, as well as published US Patent Publication No. US2009/208784. This method is facile as well as economical. A neutral monomer that can be used for reducing the density of hydrophobic or charged binding ligands can be selected from a large group of acrylic, methacrylic and acrylamide monomers such as, for example, acrylamide, hydroxypropyl acrylate, hydroxyethyl acrylate, and hydroxyethylmethacrylate. In various embodiments described herein, the neutral monomer is acrylamide.

A representative chemical structure of a binding group containing polymer, which is coated onto a solid support, is depicted in Formula A. In order for the polymer to be coated, it is generally cross-linked to other polymers. In Formula A, the polymeric structure is shown in which $R^1$ is any aliphatic or aromatic organic residue containing a hydrophobic or cation-exchange group, such as e.g., hydrophobic aliphatic or aromatic organic group selected from the group consisting of ethyl, butyl, hexyl, 2-ethylhexyl, dodecyl, stearyl, hydroxypropyl, phenyl and benzyl or cation-exchange group selected from sulfonic, sulfate, phosphoric, phosphonic or carboxylic group; $R^2$ is any uncharged aliphatic or aromatic organic linker such as e.g. acrylates, acrylamides, methacrylates, vinyl ethers and styrenics between any two or more polymeric chains.

In the polymeric structure depicted in Formula A, x, y, and z are average molar fractions of each monomer in the polymer and range independently from about 0.01 to 0.99; and m denotes attachment of a second polymer via the linker.

A representative chemical structure of a binding group containing polymer, which is grafted to a solid support, is depicted in Formula B. In Formula B, the polymeric structure is shown in which $R^1$ is any aliphatic or aromatic organic residue containing a hydrophobic or cation-exchange group, such as e.g., hydrophobic aliphatic or aromatic organic group selected from the group consisting of ethyl, butyl, hexyl, 2-ethylhexyl, dodecyl, stearyl, hydroxypropyl, phenyl and benzyl or a cation-exchange group selected from sulfonic, sulfate, phosphoric, phosphonic or carboxylic group.

In the polymeric structure depicted in Formula B, x and y are the average molar fractions of each monomer in the polymer and range independently from about 0.01 to 0.99.

In some embodiments, the polymer containing binding groups (e.g., hydrophobic binding groups) is a block copolymer, meaning that it includes a long string or block of one type of monomer followed by a long string or block of a different type of monomer.

In other embodiments, the co-polymer containing binding groups contains the monomers in a random order.

In yet other embodiments, the co-polymer containing binding groups is an alternating copolymer, where each monomer is always adjacent to two monomers of a different kind on either side.

In other embodiments, the co-polymer containing binding groups (e.g., hydrophobic binding groups) contains the monomers in a random order.

In other embodiments, the co-polymer containing binding groups is an alternating copolymer, whereas each monomer is always adjacent to two monomers of a different kind.

IV. Devices Incorporating the Compositions Described Herein

In some embodiments, compositions described herein are incorporated into devices. Suitable devices for solid supports, such as microporous membranes, include filtration cartridges, capsules, and pods. Exemplary devices also include stacked-plate filtration cartridges disclosed in the U.S. Publication Nos. US20100288690 A1 and US20080257814 A1, incorporated by reference herein. In case of these devices, a solid support is permanently bonded to the polymeric housing and the devices have a liquid inlet, an outlet, and a vent opening, and further minimize the volume of retained liquid. Other exemplary devices include pleated filter cartridges and spiral-wound filter cartridges. Yet other exemplary devices are chromatography columns. Chromatography columns can be produced from a number of suitable materials, such as glass, metal, ceramic, and plastic. These columns can be packed with solid support by the end user, or can also be pre-packed by a manufacturer and shipped to the end user in a packed state.

V. Methods of Using the Compositions and Devices Described Herein

The devices containing compositions described herein can be used for removal of protein aggregates in a flow-through mode. Prior to application for preparative scale separation, the process must be developed and validated for proper solution conditions such as pH and conductivity, and the range of protein loading on the device must be determined. The methods for process development and validation are widely known and routinely practiced in the industry.

The devices are commonly flushed, sanitized, and equilibrated with an appropriate buffer solution prior to use. Protein solution is adjusted to a desirable conductivity and pH and is subsequently pumped through a device at either constant pressure or constant flow. The effluent can be collected and analyzed for the protein yield and aggregate concentration.

In some embodiments, a device for aggregate removal, as described herein, is connected directly to a virus filtration device that is designed to ensure size-based removal of viral particles, for example, as taught in U.S. Pat. No. 7,118,675, incorporated by reference herein in its entirety.

Embodiments are further illustrated by the following examples which should not be construed as limiting. The contents of all references, patents and published patent applications cited throughout this application, as well as the Figures, are incorporated herein by reference.

Example 1. Preparation of Acrylamide-Containing Negatively Charged Filter and Comparison to Filters Containing Dimethylacrylamide This experiment demonstrates the unexpected benefit of adding acrylamide as a co-monomer to prepare adsorptive membranes used for removing impurities such as protein aggregates.

A series of cation-exchange (CEX) surface-modified membranes are prepared with binding groups, which in this case are negatively charged sulfonic acid residues. The CEX density is controlled by formulation of the reactive solution used for the surface modification. In order to evaluate the effect of the uncharged reactive co-monomer used to achieve the lower CEX density, the uncharged reactive monomers acrylamide (AM), N, N-dimethylacrylamide (DMAM), benzylmethacrylate (BMA), or isooctylacrylate (IOA), N-(2-hydroxypropyl)methacrylamide (HPMAM) are added in different amounts to the reactive solutions. The co-monomers are selected to cover a variety in size and degree of hydrophobicity or hydrophilicity.

A series of aqueous or water:acetonitrile (50:50) solutions are prepared containing the CEX monomer 2-acrylamido-2-methylpropanesulfonic acid (AMPS) ranging from 1.5 to 2.5% wt., with either AM, DMAM, BMA, IOA, or HPMAM and the fixed mass percents of the cross-linker N, N'-methylenebisacrylamide (0.8% wt.) and UV initiator Irgacure 2959 (0.2% wt.), (2-hydroxy-1-[4-(2-hydroxyethoxy)phenyl]-2-methyl-1-propanone). A hydrophilic polyvinylidene difluoride (PVDF) membrane with pore size rating of 0.10 µm and thickness of 0.100 mm is cut into square pieces of 14 cm by 14 cm and each piece is submerged in one of solutions for 30 seconds to ensure complete wetting. The excess solution is removed and the membrane is exposed to UV radiation. The membrane is subsequently rinsed with deionized water and dried in air. Table I lists the variants of CEX surface modified membranes that are prepared to evaluate the effect of the co-monomer.

TABLE 1

Mass throughputs of a virus retention filter, Viresolve Pro (VPro), using new adsorptive membranes as prefilters.

| Membrane Sample No. | Description | AMPS (wt %) | Co-monomer (wt %) | MBAM % | Mass Throughput @ V75 (kg/m2) |
|---|---|---|---|---|---|
| 1 | Virus filter only | NA | NA | NA | 0.10 |
| 2 | Base Membrane | NA | NA | NA | 0.67 |
|   |   |   | AM (%) |   |   |
| 3 | 1.8% AMPS, 3.0% AM | 1.8 | 3.0 | 0.8 | 1.50 |
|   |   |   | DMAM (%) |   |   |
| 4 | 1.5% AMPS, 3.3% DMAM | 1.5 | 3.3 | 0.8 | 0.64 |
| 5 | 1.8% AMPS, 3.0% DMAM | 1.8 | 3.0 | 0.8 | 0.94 |

TABLE 1-continued

Mass throughputs of a virus retention filter, Viresolve Pro (VPro). using new adsorptive membranes as prefilters.

| Membrane Sample No. | Description | AMPS (wt %) | MBAM % | Mass Throughput @ V75 (kg/m2) |
|---|---|---|---|---|
| 6 | 2.1% AMPS, 2.7% DMAM | 2.1 | 2.7 | 0.8 | 0.56 |
| 7 | 2.4% AMPS, 2.4% DMAM | 2.4 | 2.4 | 0.8 | 0.70 |
| 8 | 4.8% AMPS, 0% DMAM | 4.8 | 0.0 | 0.8 | 0.35 |
| | | | BMA (%) | | |
| 9 | 1.5% AMPS, 3.3% BMA | 1.5 | 3.3 | 0.8 | 0.64 |
| 10 | 1.8% AMPS, 3.0% BMA | 1.8 | 3.0 | 0.8 | 0.60 |
| 11 | 2.1% AMPS, 2.7% BMA | 2.1 | 2.7 | 0.8 | 0.55 |
| | | | IOA (%) | | |
| 12 | 1.8% AMPS, 3.0% IOA | 1.8 | 3.0 | 0.8 | 0.34 |
| 13 | 1.8% AMPS, 6.0% IOA | 1.8 | 6.0 | 0.8 | 0.22 |
| | | | HPMAM (%) | | |
| 14 | 1.5% AMPS, 3.3% HPMAM | 1.5 | 3.3 | 0.8 | 0.61 |
| 15 | 2.5% AMPS, 2.3% HPMAM | 2.5 | 2.3 | 0.8 | 0.56 |

Evaluation of the acrylamide-containing negatively charged prefilter and the other co-monomer containing prefilters is accomplished by determining their prefiltration performance to improve throughput of a downstream virus retention filter during filtration. The feed stream contains polyclonal IgG aggregates that generally quickly foul the virus filter which does not have a virus pre-filter upstream of the filter. Because the binding group used is negatively charged, strong CEX solution binding conditions for IgG are used to evaluate the performance of the pre-filter.

A polyclonal IgG feed for testing the protection offered by a virus filter is prepared fresh at concentration of 4.0 g/L IgG using SeraCare Life Sciences, Human Gamma Globulin Powder, (Catalog # HS-470-90) at pH 4, 10 mM sodium acetate at 2.0 mS/cm. Final pH and conductivity adjustments are made using 10 M HCl, NaOH, or 4 M NaCl and the solution is sterile-filtered prior to use.

Micro filtration devices with filtration areas of 3.1 cm$^2$ are pre-molded using 3 layers of membrane and put in series at a 1:1 area ratio with Viresolve® Pro Micro devices (EMD Millipore Corporation, Billerica, Mass.). Both devices are prewet and vented to remove air using only the buffer (pH 4, 10 mM acetate, 2 mS/cm). Under constant pressure of 30 psi, an initial flux in mL of buffer per minute is determined by measuring mass over a 20 minute period to arrive at the initial permeability value. The feed is switched to the 4 g/L polyclonal IgG feed at 30 psi and the volume throughput is measured and plotted versus time until the flux decays to 25% the initial buffer only flux. The total throughput of the polyclonal IgG solution is measured in L/m$^2$ at V75 and converted to kg of polyclonal IgG per m$^2$ of membrane.

As can be seen from Table 1 and FIG. 2, membrane 3 modified with 1.8% AMPS, 3.0% acrylamide provides greater protection for the virus removal filter (greater mass throughput) than the other combinations of AMPS and co-monomers. The acrylamide-containing membrane 3 also provides a higher mass throughput over the base membrane control membrane 2 and the non-prefiltered virus membrane 1.

Example 2. Permeability Changes in Response to Presence of Protein in Solution is Indicative of 3-Dimensional Nature of Surface Coating Containing Acrylamide This example demonstrates the nature of the surface chemistry prepared using acrylamide as a co-monomer.

Permeability of the device combinations used in Example 1 is tested using both the feed solution containing 4 g/L IgG and the identical buffer solution without any protein. It is observed that the devices containing acrylamide as a co-monomer harbor some unique properties, in that the permeability of the train increases in the presence of IgG (Table 2, FIGS. 3 & 4), as compared to permeability in case of other prefilters and un-prefiltered VPro (membrane 1). Without wishing to be bound by theory, it is hypothesized that the use of small hydrophilic co-polymerized acrylamide with the CEX binding group AMPS in membrane 3 allows for a unique polymer hydrogel (FIG. 5), which can easily contract when IgG forms ionic cross-links, thus opening the membrane pores and resulting in the increase of permeability.

The more hydrophobic formulations in Table 2 using the co-monomers BMA and DMAM (membranes 4, 5, and 9) do not have the same effect on permeability (Table 2, FIGS. 3 & 4).

TABLE 2

Permeability of buffer and protein solution of various prefilter/VPro combinations.

| Membrane Sample No. | Description | Buffer (LMH/psi) | 4 g/L IgG in Buffer (LMH/psi) |
|---|---|---|---|
| 1 | Virus filter only | 16.0 | 7.6 |
| 2 | Base membrane | 14.6 | 14.0 |
| 8 | 4.8% AMPS, 0% DMAM | 12.5 | 11.2 |
| 9 | 1.5% AMPS, 3.3% BMA | 12.3 | 11.8 |
| 4 | 1.5% AMPS, 3.3% DMAM | 8.0 | 7.4 |
| 5 | 1.8% AMPS, 3.0% DMAM | 11.4 | 11.2 |
| 3 | 1.8% AMPS, 3.0% AM | 6.1 | 8.3 |

Example 3. Protein Binding Capacity as a Function of Conductivity

This example illustrates the unique effect of acrylamide as a co-monomer by measuring the static IgG binding capacity of the surface modified membranes in Table 3 at pH 4.0 and at different solution conductivities.

A polyclonal IgG feed for measuring static binding capacities was prepared fresh at 1.0 g/L IgG using SeraCare Life Sciences, Human Gamma Globulin Powder, (Catalog # HS-470-90) in pH 4, 10 mM sodium acetate. The final pH 4.0 and conductivities in Table 3 are made using 10 M HCl, NaOH, and NaCl. The solution is sterile filtered prior to use.

Membrane samples are cut to known radii using a circular die. Membrane volume (V=$\pi r^2 h$) is calculated using membrane thickness of 100 microns. The membrane disk samples are prewet with water and exchanged into the appropriate pH 4.0 buffer solutions, as per Table 3. The membrane disks are subsequently put into the appropriate volume of 1 g/L IgG at pH 4.0. The target loadings are about 100 mg/ml for 2 mS/cm, 50 mg/ml for 15 and 25 mS/cm, and 25 mg/mL for 37 and 49 mS/cm. Membrane samples and IgG solutions are rotationally mixed for 8 hours and the supernatant is measured for final IgG concentration by UV280 absorbance. Static IgG capacities in mg IgG per mL of membrane are calculated by mass balance based on the final supernatant concentrations. The final membrane static IgG capacities in Table 3 and FIG. 6 show that membranes containing acrylamide, i.e., membranes 3 and 17 and having a Tetra (ethylene glycol) diacrylate cross-linker replacing MBAM, have higher static IgG capacities at pH 4 up to 25 mS/cm than other membranes tested (i.e., base membrane 2), membranes with a greater number of binding groups (i.e., membranes 7 and 8), membranes without acrylamide (i.e., membranes 8, 16, 18), and membranes with the co-monomer DMAM (i.e., membranes 7, 5, 19).

The presence of the small, neutral, and hydrophilic acrylamide with the CEX binding group AMPS in membranes 3 and 17 allows for a unique polymer hydrogel which provides greater static IgG capacities.

analytical size exclusion chromatography (SEC), and aggregate capacity of the membranes in Table 4.

The feed is prepared fresh at 10.0 g/L IgG using SeraCare Life Sciences, Human Gamma Globulin Powder, (Catalog # HS-470-90) in pH 4, 10 mM sodium acetate at 2.0 mS/cm (using NaCl). Final pH and conductivity adjustments are made using 10 M HCl, NaOH, or 4 M NaCl and the solution is sterile-filtered prior to use.

Micro filtration devices with filtration areas of 3.1 cm$^2$ are pre-molded using 3 layers of membrane. Devices are prewet and flushed with 20 mL of buffer solution, pH 4, 10 mM acetate, 2 mS/cm and then 40 mL of 10 g/L IgG (loading of 4.0 kg/L or 1.3 kg/m$^2$) is flowed through individual devices at 0.2 mL/min (2 CV/min) Devices are washed with 2 mL (20 CV) of buffer and eluted with 2 mL (20 CV) of pH 4, 0.5 M NaCl.

The elutions are analyzed for molecular weight species using analytical size exclusion chromatography (SEC). Percent aggregates determined from the integrations of the SEC chromatograms and IgG binding capacities (from UV280 elution concentrations) are used to calculate the aggregate capacities of the membranes in Table 4 and FIGS. 7 and 8.

FIG. 9 is a representative chromatogram of a normalized SEC-HPLC overlay including the feed loading solution and elutions from membranes 3, 16, 5, and 8 from Table 4. The overlay shows that the elution off of membrane 3 that contains acrylamide has a higher percentage of aggregates than membranes 8 and 16 without a neutral co-monomer, or membrane 5 with the co-monomer DMAM. This result demonstrates that the presence of acrylamide improves the membrane selectivity for aggregates.

TABLE 3

Static binding capacities for IgG of various CEX surface-modified membranes. Membranes 17-19 have Tetra(ethylene glycol) diacrylate cross-linker replacing N,N'-methylenebisacrylamide in membranes 3, 5, and 16.

| Membrane Sample No. | Description | Conductivity (mS/cm) Static IgG Capacity (mg/mL) | | | | |
|---|---|---|---|---|---|---|
| | | 2 | 15 | 25 | 37 | 49 |
| (2) | Base Membrane | 5.2 | 1.7 | 2.6 | 0.8 | 0.7 |
| (8) | 4.8% AMPS, 0% DMAM | 20.6 | 15.7 | 9.9 | 5.2 | 3.4 |
| (7) | 2.4% AMPS, 2.4% DMAM | 41.0 | 23.0 | 10.4 | 1.6 | 0.5 |
| (3) | 1.8% AMPS, 3.0% AM | 57.0 | 34.4 | 15.7 | 3.0 | 1.0 |
| (16) | 1.8% AMPS, 0% AM | 10.5 | 7.8 | 6.2 | 3.2 | 2.2 |
| (5) | 1.8% AMPS, 3.0% DMAM | 12.3 | 8.6 | 4.1 | 0.9 | 0.5 |
| (17) | 1.8% AMPS, 3.0% AM (TEGDA) | 30.8 | 22.9 | 5.3 | 1.0 | 0.5 |
| (18) | 1.8% AMPS, 0% AM (TEGDA) | 11.7 | 9.2 | 2.5 | 2.8 | 2.3 |
| (19) | 1.8% AMPS, 3.0% DMAM (TEGDA) | 14.3 | 6.2 | 3.1 | 1.2 | 0.8 |

Example 4. Selectivity of Acrylamide-Containing Membranes for Protein Aggregates, as Assessed by SEC Measurements of Elutions from CEX Dynamic Binding This example demonstrates selectivity of acrylamide-containing membranes for IgG aggregates.

The dynamic CEX aggregate capacity is measured for the membranes in Table 3 to quantify the aggregate selectivity differences of the membranes. A polyclonal IgG feed containing aggregates is used to provide equivalent dynamic CEX loadings under binding conditions to membranes in Table 3. The CEX elutions after equivalent loading are used to determine the IgG capacity, aggregate selectivity by Aggregate capacities in Table 4 and FIGS. 7 and 8 are highest for the acrylamide-containing membranes 3 and 17 (with a Tetra(ethylene glycol) diacrylate cross-linker replacing MBAM). Membranes containing acrylamide have higher aggregate capacities than the base membrane 2, membranes with a greater number of binding groups (membranes 8 and 7), membranes without acrylamide (membranes 8, 16, 18) as well as membranes with DMAM (membranes 7, 5, 19).

FIG. 8 demonstrates that membranes with higher aggregate capacities tend to provide better Viresolve® Pro protection, thereby yielding higher IgG mass throughputs using the process in Example 1.

TABLE 4

Aggregate binding capacities for IgG of various CEX surface-modified membranes.

| Membrane Sample No. | Description | Aggregate Capacity (mg/mL) | Mass Throughput @ V75 (k/m2) |
|---|---|---|---|
| (2) | Base Membrane | 2.6 | 0.53 |
| (8) | 4.8% AMPS, 0% DMAM | 5.8 | 0.33 |
| (7) | 2.4% AMPS, 2.4% DMAM | 9.4 | 0.60 |
| (3) | 1.8% AMPS, 3.0% AM | 10.3 | 0.71 |
| (16) | 1.8% AMPS, 0% AM | 3.7 | 0.42 |
| (5) | 1.8% AMPS, 3.0% DMAM | 3.7 | 0.56 |
| (17) | 1.8% AMPS, 3.0% AM (TEGDA) | 12.0 | 1.19 |
| (18) | 1.8% AMPS, 0% AM (TEGDA) | 3.5 | 0.34 |
| (19) | 1.8% AMPS, 3.0% DMAM (TEGDA) | 4.2 | 0.54 |

Example 5. Preparation and Testing of Acrylamide-Containing Hydrophobic Prefilter in Comparison to Prefilters without Acrylamide This example demonstrates the benefits of using acrylamide as a co-monomer with a hydrophobic binding group for protecting a virus filter under hydrophobic binding conditions (neutral to higher pH and moderate to high conductivity).

The hydrophobic monomer N-Benzylacrylamide, 2.5% wt (Alfa Aesar L11450) is used as the binding group and copolymerized with 2.0 wt % acrylamide and the cross-linker N, N'-methylenebisacrylamide (0.8% wt.). The monomers are dissolved in 50:50 water: MPD ((±)-2-Methyl-2, 4-pentanediol), a 14×14 cm sheet of 0.22 micron rated hydrophilic polyethersulfone (PES) membrane is dipped in the solution for 30 seconds, and the excess solution is removed. The polymerization is initiated using electron beam (2.5 MRad @ 170 kV) and the membrane is subsequently rinsed with deionized water and dried in air. The prefilter membranes with a hydrophobic binding group with and without the acrylamide co-monomer are evaluated for their prefiltration performance to improve throughput of a downstream virus filter. The feed stream contains polyclonal IgG aggregates that generally quickly foul the non-prefiltered Virus filter (Example 1). Since the binding group is hydrophobic, its effect with and without acrylamide is evaluated under solution conditions of neutral to higher pH and moderate to high conductivity, that generally enhance hydrophobic interactions of antibodies.

A polyclonal IgG feed is prepared fresh at 0.5 or 2.0 g/L IgG SeraCare Life Sciences, Human Gamma Globulin Powder, (Catalog # HS-470-90) at pH 7.0, 5 mS/cm, pH 7.5, 15 mS/cm, and pH 6.0, 25 mS/cm using Tris buffer and NaCl (Table 5). Final pH and conductivity adjustments are made using 10 M HCl, NaOH, or 4 M NaCl and the solution is sterile-filtered prior to use.

Micro filtration devices with filtration area 3.1 cm² are pre-molded using 3 layers of membrane and put in series at a 1:1 area ratio with Viresolve® Pro Micro devices (EMD Millipore Corporation, Billerica, Mass.). Both devices are prewet and vented to remove air using buffer solution. Under constant pressure of 30 psi, an initial flux in mL/min is measured by mass over a 20 minute period to determine an initial constant flux value. The feed is switched to the polyclonal IgG solution at 30 psi and the volume throughput is measured and plotted versus time until the flux decayss to 25% the initial buffer flux. The total throughput of the polyclonal IgG solution is measured in L/m² at V75 and converted to kg of polyclonal IgG per m² membrane. As can be seen from Table 5 and FIGS. 10, 11, and 12, membranes 3 and 4 modified with 2.5% BAM, 1.0 or 2.0% acrylamide provide greater protection of the virus removal filter (greater mass throughput) than membranes 5, 6, 7, or 8 which did not contain acrylamide. The acrylamide-containing membranes 3 and 4 also provide similar mass throughput to the Viresolve® Prefilter (primarily hydrophobic mechanism) and much better throughput than the Viresolve® Shield (CEX mechanism) under the 3 solution conditions.

TABLE 5

Formulation and performance of acrylamide-containing hydrophobic prefilters in comparison to currently available commercial prefilters and prefilters without acrylamide.

| Membrane Sample No. | Description | N-Benzylacrylamide (wt %) | Acrylamide (wt %) | MBAM % | Mass Throughput @ V75 (kg/m2) | | |
|---|---|---|---|---|---|---|---|
| | | | | | pH 7.0 5 mS/cm | pH 7.5 15 mS/cm | pH 6.0 25 mS/cm |
| (1) | Viresolve Shield | NA | NA | NA | 0.24 | 0.09 | 0.12 |
| (2) | Viresolve Prefilter | NA | NA | NA | 0.71 | 0.51 | 0.48 |
| (3) | 2.5% BAM, 2.0% AM | 2.5 | 2.0 | 0.8 | 0.63 | 0.39 | 0.46 |
| (4) | 2.5% BAM, 1.0% AM | 2.5 | 1.0 | 0.8 | | 0.39 | 0.48 |
| (5) | 2.0% BAM | 2.0 | 0 | 0.8 | 0.19 | 0.21 | 0.24 |
| (6) | 3.0% BAM | 3.0 | 0 | 0.8 | 0.23 | 0.19 | 0.16 |
| (7) | 5.0% BAM | 5.0 | 0 | 0.8 | | | 0.19 |
| (8) | 2.5% BAM, 3.0% MBAM | 2.5 | 0 | 3.0 | 0.32 | | |

Example 6. Comparison of Acrylamide-Containing Hydrophobic Prefilter to Commercial Prefilters and Unmodified Base Membranes Using Polyclonal IgG This example demonstrates that the membrane (3) from Example 5 (Table 5) with the surface modification chemistry of the hydrophobic binding ligand N-Benzylacrylamide (BAM) and acrylamide (AM) protects a virus filter under hydrophobic binding conditions (neutral to higher pH and moderate to high conductivity). As observed, membrane (3) improves the polyclonal IgG mass throughput of a downstream virus filter (Viresolve® Pro, EMD Millipore Corp., Billerica, Mass.) better than commercially available prefilters and unmodified base polymer membranes.

The prefilters in Table 6 were evaluated for their prefiltration performance to improve the polyclonal IgG mass throughput of a downstream virus filter. Membrane sample (1) is Viresolve® Shield, a membrane filter with a CEX mechanism based surface modification (VPMSKITNB9, EMD Millipore Corporation, Billerica, Mass.). Sample (2) is OptiScale-40 Viresolve® Prefilter, a hydrophobic mechanism based depth filter (SSPVA40NM9, EMD Millipore Corporation, Billerica, Mass.) with a filtration area of 5 cm².

Membrane (4) is a hydrophilized polyethersulfone (PES) 0.2 μm membrane (Express Sterilizing Grade, GEPP, EMD Millipore Corporation, Billerica, Mass.) with a thickness of 110 μm. Membrane (5) is a hydrophilic nylon (polyamide) 0.20 μm membrane (GNWP, EMD Millipore Corporation, Billerica, Mass.) with a thickness of 170 μm. Membrane (6) is an unmodified polyethersulfone (PES) 0.2 μm membrane (GEHP, EMD Millipore Corporation, Billerica, Mass.) with a thickness of 110 μm.

(greater mass throughput of polyclonal IgG) than the commercial membrane filters (1) and (4) as well as the unmodified base polymer membranes (5) and (6). This demonstrated that the surface modification using the hydrophobic ligand BAM co-polymer with acrylamide protected better under typical hydrophobic binding conditions (pH 6, 25 mS/cm) than the commercial membrane filters (1), CEX mechanism and (4), hydrophilized PES, as well as the unmodified membranes composed of polyamide (5) and polyethersulfone (6). Membrane (3) provided greater mass throughput to Sample (2) the Viresolve® Prefilter (EMD Millipore Corp., Billerica, Mass.) when normalized to 3.1 cm², which is known to adsorb proteins primarily through a hydrophobic mechanism.

TABLE 6

Acrylamide-containing hydrophobic prefilter in comparison to currently available commercial prefilters and unmodified base membranes

| Membrane Sample No. | Description | N-Benzylacrylamide (wt %) | Acrylamide (wt %) | MBAM % | Mass Throughput (kg/m2) | |
|---|---|---|---|---|---|---|
| | | | | | V75 | V90 |
| (1) | Viresolve Shield | NA | NA | NA | 0.05 | 0.05 |
| (2) | Viresolve Prefilter | NA | NA | NA | 0.50 | 0.54 |
| (3) | 2.5% BAM, 2.0% AM | 2.5 | 2.0 | 0.8 | 0.63 | 0.74 |
| (4) | 0.2 μm Sterilizing grade membrane (hydrophilized Polyethersulfone, PES) | NA | NA | NA | 0.08 | 0.10 |
| (5) | 0.2 μm Polyamide membrane | NA | NA | NA | 0.36 | 0.40 |
| (6) | 0.2 μm Polyether sulfone (PES) membrane | NA | NA | NA | 0.13 | 0.14 |

The feed stream contains polyclonal IgG aggregates that quickly foul the non-prefiltered virus filter (Example 1). Since the binding group of membrane (3) is hydrophobic, its prefiltration performance was evaluated under solution conditions that generally enhance hydrophobic interactions of antibodies—neutral to higher pH and moderate to high conductivity.

A polyclonal IgG feed is prepared fresh at 2.0 g/L IgG SeraCare Life Sciences, Human Gamma Globulin Powder, (Catalog # HS-470-90) at pH 6.0, 25 mS/cm using acetate buffer and NaCl. Final pH and conductivity adjustments are made using 10 M HCl, NaOH, or 4 M NaCl and the solution is sterile-filtered prior to use.

Micro filtration devices with filtration area of 3.1 cm² were pre-molded using 2 or 3 layers of membrane to get equivalent thicknesses or total volume and put in series at a 1:1 area ratio with the virus filtration devices Viresolve® Pro Micro (EMD Millipore Corporation, Billerica, Mass.). Both devices were prewet and vented to remove air using buffer solution. Under constant pressure of 30 psi, a buffer only initial flux in mL/min was measured by mass over a 20 minute period to determine an initial constant flux value. The feed was switched to the polyclonal IgG in buffer solution at 30 psi and the volume throughput was measured and plotted versus time until the flux decayed to 25% and 10% the initial buffer flux. The total throughput of the polyclonal IgG solution was measured in L/m² at V75 and V90 and converted to kg of polyclonal IgG per m² membrane.

As can be seen in Table 6 and FIG. 13, the membrane (3) modified with 2.5% BAM, 2.0% Acrylamide, 0.8% MBAM provided greater protection of the virus removal filter Example 7. Acrylamide-Containing Hydrophobic Prefilter Performance with Monoclonal Antibodies This example demonstrates that membrane (3) from Example 6 (Table 6) with the surface modification chemistry of the hydrophobic binding ligand N-Benzylacrylamide (BAM) with Acrylamide (AM) protects a virus filter (Viresolve® Pro, EMD Millipore Corp., Billerica, Mass.) under hydrophobic binding conditions to improve the mass throughput of monoclonal antibodies (MAbs). These examples demonstrated prefiltering the virus filter with membrane (3) performed better than virus filtration without prefiltration, using an unmodified membrane prefilter composed of polyamide (5) or a hydrophilized PES membrane (4).

The membrane prefilters (3), (4), and (5) in Table 7 were evaluated for their prefiltration performance to improve the mass throughput of monoclonal antibodies (MAbs) with a downstream virus filter (Viresolve® Pro, EMD Millipore Corp., Billerica, Mass.) under hydrophobic binding conditions (neutral to higher pH and moderate to high conductivity).

Membrane (4) is a hydrophilized polyethersulfone (PES) 0.2 μm membrane (Express Sterilizing Grade, GEPP, EMD Millipore Corp., Billerica, Mass.) with a thickness of 110 μm. Membrane (5) is a hydrophilic nylon (polyamide) 0.20 μm membrane (GNWP, EMD Millipore Corp., Billerica, Mass.) with a thickness of 170 μm.

Specifics of the MAb feed streams MAb 01, 05, and 07 and filtration capacity experiment conditions and results are detailed in Table 7, FIGS. 14-16. The three MAbs were all purified to a state of at least post Protein A elution and solution conditions were adjusted to the Table 7 conditions using 10 M HCl, NaOH, or 4 M NaCl.

Stainless steel Swinney 13 mm diameter filter holders with a filtration area of 0.8 cm$^2$ (XX3001200, EMD Millipore Corp., Billerica, Mass.) were assembled using 2 or 3 layers of prefiltration membrane (3), (4), and (5) to get equivalent thicknesses or total volume and put in series at a 1:1 area ratio using the same holder with 2 layers of Viresolve® Pro virus filtration membrane (EMD Millipore Corp., Billerica, Mass.).

Prefilter and virus membrane devices were prewet with buffer at 30 psi and transferred to the monoclonal antibody feeds for testing. The capacity experiments were run at constant flow of 166 LMH (L/m2·hr) and pressure was monitored on the upstream side of the filtration to detect plugging of the filtration trains. The total throughput of the MAb solutions were measured in volume and converted to kg of MAb per m$^2$ of virus membrane.

The three examples using three different MAbs were all under more favorable hydrophobic binding conditions (neutral to higher pH and moderate to high conductivity), near the Isoelectric points of the MAbs and/or moderate solution conductivities.

FIG. 14 shows membrane (3) is effective at reducing the pressure increase compared to the non-prefiltered VPro. FIG. 15 shows membrane (3) protects VPro to improve mass throughput 4× of MAb 05 compared to non-prefiltered VPro. FIG. 16 shows for MAb 07 membrane (3) performed better than VPro virus filtration without prefiltration, and unmodified membrane prefilters composed of polyamide (5), and the commercial sterilizing grade membrane filter (4).

so forth used in the specification, including claims, are to be understood as being modified in all instances by the term "about." Accordingly, unless otherwise indicated to the contrary, the numerical parameters are approximations and may vary depending upon the desired properties sought to be obtained by the embodiments disclosed herein. Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the disclosure being indicated by the following claims.

What is claimed is:

1. A method of separating a monomeric protein of interest from protein aggregates in a sample by porous membrane filtration, the method comprising contacting the sample with a porous membrane comprising a cross-linked coating comprising a co-polymer of benzyl acrylamide, acrylamide and N,N'-methylenebisacrylamide, wherein the membrane selectively binds protein aggregates, thereby separating the monomeric protein of interest from the protein aggregates.

2. The method of claim 1 wherein the method is performed at neutral to higher pH of 6 or greater.

TABLE 7

Monoclonal antibody virus filtration performance using Acrylamide-containing hydrophobic prefilter (3) compared to commercial membranes

| FIG. # | MAb | Concentration (g/L) | Aggregates SEC-HPLC (%) | pH | Conductivity (mS/cm) | Prefilter | Mass Throughput @ 30 psi (kg/m2) |
|---|---|---|---|---|---|---|---|
| 13 | 01 | 15.3 | 0.8 | 7.0 | 4.2 | (3) 2.5% BAM, 2.0% AM | >7.5 |
|  |  |  |  |  |  | None (VPro only) | >7.5 |
| 14 | 05 | 9.2 | 0.4 | 7.5 | 18.0 | (3) 2.5% BAM, 2.0% AM | 1.2 |
|  |  |  |  |  |  | None (VPro only) | 0.3 |
| 15 | 07 | 7.0 | 4.0 | 8.0 | 8.0 | (3) 2.5% BAM, 2.0% AM | >3.1 |
|  |  |  |  |  |  | None (VPro only) | 1.0 |
|  |  |  |  |  |  | (5) 0.2 µm Polyamide membrane | 2.9 |
|  |  |  |  |  |  | (4) 0.2 µm Polyether sulfone (PES) membrane (hydrophilized) | 1.6 |

In summary, the newly discovered membrane chemistries enable significant improvements in the performance of prefilters for protection of virus filters.

The specification is most thoroughly understood in light of the teachings of the references cited within the specification which are hereby incorporated by reference. The embodiments within the specification provide an illustration of embodiments and should not be construed as limiting in scope. The skilled artisan readily recognizes that many other embodiments are encompassed by this disclosure. All publications and reference materials are incorporated by reference in their entirety. To the extent that the material incorporated by reference contradicts or is inconsistent with the present specification, the present specification will supercede any such material. The citation of any references herein is not an admission that such references are prior art.

Unless otherwise indicated, all numbers expressing quantities of ingredients, cell culture, treatment conditions, and 3. The method of claim 1 wherein the method is performed in a solution of moderate to high conductivity of 5 mS/cm or greater.

4. The method of claim 1, wherein the protein aggregates are selected from the group consisting of dimers, trimers, and tetramers.

5. The method of claim 1, wherein the aggregates are pentamers and higher.

6. The method of claim 1, wherein the monomeric protein of interest is an antibody.

7. The method of claim 6, wherein the antibody is a monoclonal antibody.

8. The method of claim 1, wherein the monomeric protein of interest is a recombinant protein.

9. The method of claim 1, wherein the monomeric protein of interest is a polyclonal antibody.

10. The method of claim 1, wherein the monomeric protein of interest is further subjected to filtration through a virus-retentive filter.

\* \* \* \* \*